US005859227A

United States Patent [19]
Giordano et al.

[11] Patent Number: 5,859,227
[45] Date of Patent: Jan. 12, 1999

[54] RNA SEQUENCES WHICH INTERACT WITH RNA-BINDING PROTEINS

[75] Inventors: Tony Giordano, Phoenixville, Pa.; Deborah L. Beach, Wilmington, Del.; David Jacobs, Gurnee, Ill.

[73] Assignee: Bearsden Bio, Inc., Frazer, Pa.

[21] Appl. No.: 803,260

[22] Filed: Feb. 20, 1997

Related U.S. Application Data

[63] Continuation-in-part of Ser. No. 690,010, Jul. 31, 1996.
[51] Int. Cl.$^6$ ............................. C07H 21/02; C07H 21/04
[52] U.S. Cl. .......................................... 536/24.1; 536/23.1
[58] Field of Search ................................. 536/23.1, 24.1, 536/24.3

[56] References Cited

U.S. PATENT DOCUMENTS

| | | | |
|---|---|---|---|
| 3,625,214 | 12/1971 | Higuchi | 128/260 |
| 4,789,734 | 12/1988 | Pierschbacher | 530/395 |
| 4,906,474 | 3/1990 | Langer et al. | 424/428 |
| 4,925,673 | 5/1990 | Steiner et al. | 424/455 |

OTHER PUBLICATIONS

Birnbaum et al., Proc. Natl. Acad. Sci. USA 83, 5784–5788 (1986).
Luskey, Mol. Cell. Biol. 7(5), 1881–1893 (1987).
Luskey et al., J. Biol. Chem. 260(18), 10271–10277 (1985).
Aso et al., Biochem. Biophys. Res. Comm. 174(1), 222–227 (1991).
Hall et al., J. Immunol. 141(8), 2781–2787 (1988).
Jain et al., Nucleic Acids Symp. Ser. 33, 209–211 (1995)(abstract only).
Jain et al., Mol. Cell. Biol. 17(2), 954–962 (1997 Feb.).
Ashley, C.T., et al. "FMR1 Protein: Conserved RNP Family Domains and Selective RNA Binding" *Science* 262:563–566 (Oct. 1993).
Smith, J.A. Analysis of Proteins: *Current Protocols in Molecular Biology* 2:Supp. 21.
Baer, M.L., et al. "Specific RNA Binding by Amino–terminal Peptides of Alfalfa Mosaic Virus Coat Protein" *The EMBO Journal* 13(3):727–735 (1994).
Bass, B.L. "Double–Stranded RNA Binding Proteins and Their Substrates" *Nucleic Acids Symposium Series No. 13* 13–15.
Bohjanen, P.R., et al. "An Inducible Cyotoplasmic Factor (AU–B) Binds Selectively to AUUUA Multimers in the 3' Untranslated Region of Lymphokine mRNA" *Mol. Cell. Biol.* 11(6):3288–3295 (Jun. 1991).
Brewer, G. "An A +U–Rich Element RNA–Binding Factor Regulates c–myc mRNA Stability in Vitro" *Mol. Cell. Biol.* 11(5):2460–2466 (May 1991).
Burd and Dreyfuss, "Conserved structures and diversity of functions of RNA–binding proteins" Science 265:615–621 (1994).
Carey, J. and Uhlenbeck, O. "Kinetic and Thermodynamic Characterization of the R17 Coat Protein–Ribonucleic Acid Interaction" *Biochemistry* 22:2610–2615 (1983).

Eberwine, J.H., et al. "mRNA Structure, In Situ, as Assessed by Microscopic Techniques" *Microscopy Research and Technique* 25:19–28 (1993).
Gillis, P. and Malter, J. "The Adenosine–Uridine Binding Factor Recognizes the AU–rich Elements of Cytokine, Lymphokine, and Oncogene mRNAs*" *J. Biol. Chem.* 266(5):3172–3177 (1991).
Görlach, M., et al. "The Determinants of RNA–binding Specificity of the Heterogeneous Nuclear Ribonucleoprotein C Proteins*" *J. Biol. Chem.* 269(37):23074–23078 (Sep. 1994).
G. Gregoriadis, Chapter 14. "Liposomes", *Drug Carriers in Biology and Medicine* pp. 287–341 (Academic Press, 1979).
Hamilton, B.J. "Association of Heterogeneous Nuclear Ribonucleoprotein A1 and C Proteins with Reiterated AUUUA Sequences*" *J. Biol. Chem.* 268(12):8881–8887 (Apr. 1993).
Henics, T., et al. "Combined Application of In Vivo UV–Crosslinking and In Vitro Label, Transfer in the Examination of AU–Rich Sequence Binding Protein—RNA Interactions" *Cell Biology International* 19(9):791–801 (1995).
Herbert, A., et al. "Chicken Double–strranded RNA Adenosine Deaminase has Apparent Specificity of Z–DNA" *Proc. Natl. Acad. Sci. USA* 92:7550–7554 (Aug. 1995).
Hoy and Schimke, "Bromodeoxyuridine/DNA Analysis of Replication in CHO Cells After Exposure to UV Light" *Mutation Research*, 290:217–230 (1993).
Johnstone and Thorpe, *Immunochemistry in Practice* (Blackwell Scientific Publications, 1987).
Kerkhof, L. "A Comparison of Substrates for Quantifying the Signal from a Nonradiolabeled DNA Probe" *Analytical Biochemistry* 205:359–364 (1992).
Kiledjian, M., et al. "Identification of Two KH Domain Proteins in the $\alpha$–globin mRNP Stability Complex" *The EMBO Journal* 14(17):4357–4364 (1995).
Langer, et al. "Enzymatic Synthesis of Biotin–Labeled Polynucleotides: Novel Nucleic Acid Affinity Probes," *Proc. Natl. Acad. Sci. USA*, 78:6633 (1981).
Malter, J. "Identification of an AUUUA–Specific Messenger RNA Binding Protein" *Science* 246:664–666 (Nov. 1989).
Neupert, B., et al. "A High Yield Affinity Purification Method for Specific RNA–binding Proteins: Isolation of the Iron Regulatory Factor from Human Placenta" *Nucleic Acids Research* 18(1):51–55 (1990).
Oberste, M.S. and Flanegan, J.B. "Measurement of Poliovirus RNA Polymerase Binding to Poliovirion and Nonviral RNAs Using a Filter–binding Assay" *Nucleic Acids Research* 16(21):10339–10352 (1988).

(List continued on next page.)

*Primary Examiner*—Kenneth R. Horlick
*Attorney, Agent, or Firm*—Arnall Golden & Gregory, LLP

[57] ABSTRACT

Disclosed is a method for identifying possible binding sites for RNA binding proteins in nucleic acid sequences, and confirming the identity of such prospective binding sites by detection of interaction between the prospective binding site and RNA binding proteins. Also disclosed are specific binding sites of RNA binding proteins which have been identified using this method.

7 Claims, 3 Drawing Sheets

OTHER PUBLICATIONS

Rouault et al., "The iron–responsive element binding protein: A method for the affinity purification of a regulatory RNA–binding protein." Proc. Natl. Acad. Sci. USA 86:5768–5772 (1989).

Rondon, I.J., et al. "Hypoxia Up–regulates the Activity of a Novel Erythropoietin mRNA Binding Protein*" *J. Bio. Chem.* 266(25):16594–16598 (Sep. 1991).

Sambrook, J., et al. *Molecular Cloning Cold* Spring Harbor Laboratory Press $2^{nd}$ Ed. (1989).

Scripture, J.B. and Huber, P.W. "Analysis of the Binding of *Xenopus* Ribosomal Protein L5 to Oocyte 5 S rRNA" *J. Bio. Chem.* 270(45):27358–27365 (Nov. 1995).

Shen, Q., et al. "RNA–binding Proteins That Specifically Recognize the Selenocysteine Insertion Sequence of Human Cellular Glutathione Peroxidase mRNA*" *J. Bio. Chem.* 270(51):30448–30452 (Dec. 1995).

Wansink, D.G., et al. "Fluorescent Labeling of Nascent RNA Reveals Transcription by RNA Polymerase II in Domains Scattered Throughout the Nucleus" *J. Cell Bio.* 122(2):283–293 (Jul. 1993).

Yu, et al., "Cyanine Dye dUTP Analogs for Enzymatic Labeling of DNA Probes," *Nucleic Acids Res.*, 22:3226–3232 (1994).

Zaidi, S.H.E. and Malter, J.S. "Amyloid Precursor Protein mRNA Stability is Controlled by a 29–Base Element in the 3'–Untranslated Region*" *J. Bio. Chem.* 269(39):24007–24013 (Sep. 1994).

Zaidi, S.H.E., et al "Multiple Proteins Interact at a Unique *cis*–Element in the 3'–Untranslated Region of Amyloid Precursor Protein mRNA*" *J. Biol. Chem.* 269(39):24000–24006 (Sep. 1994).

Zhang, W., et al "Purification, Characterization, and cDNA Cloning of an AU–Rich Element RNA–Binding Protein, AUF1" *Mol. Cell. Bio.* 13(12):7652–7665 (Dec. 1993).

IRE

U1

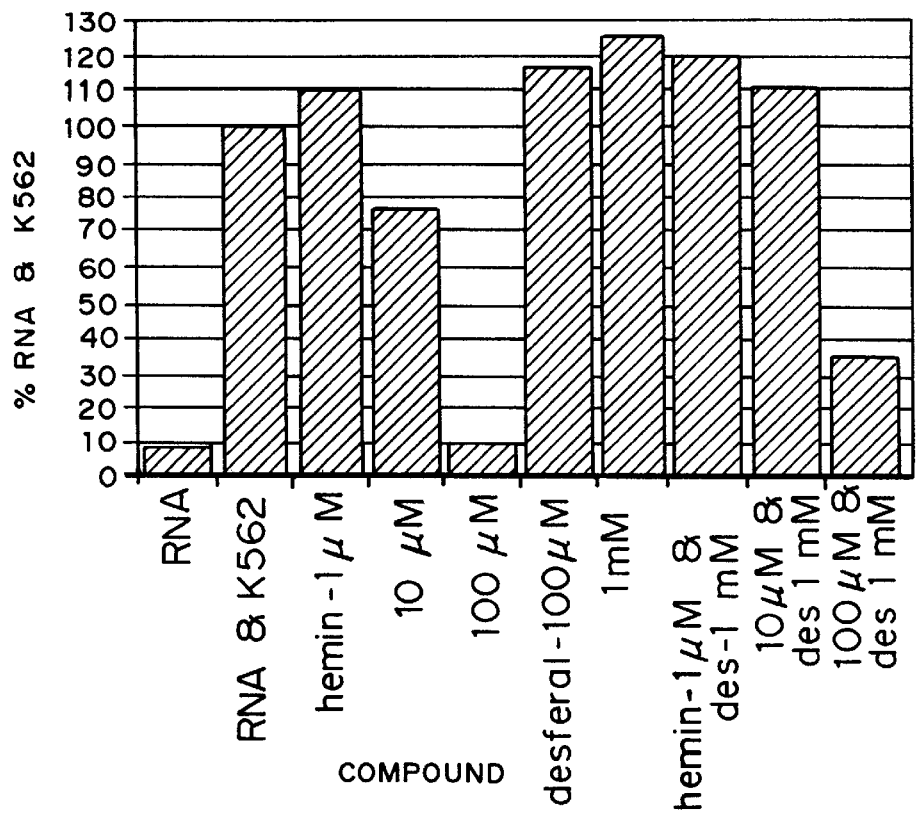
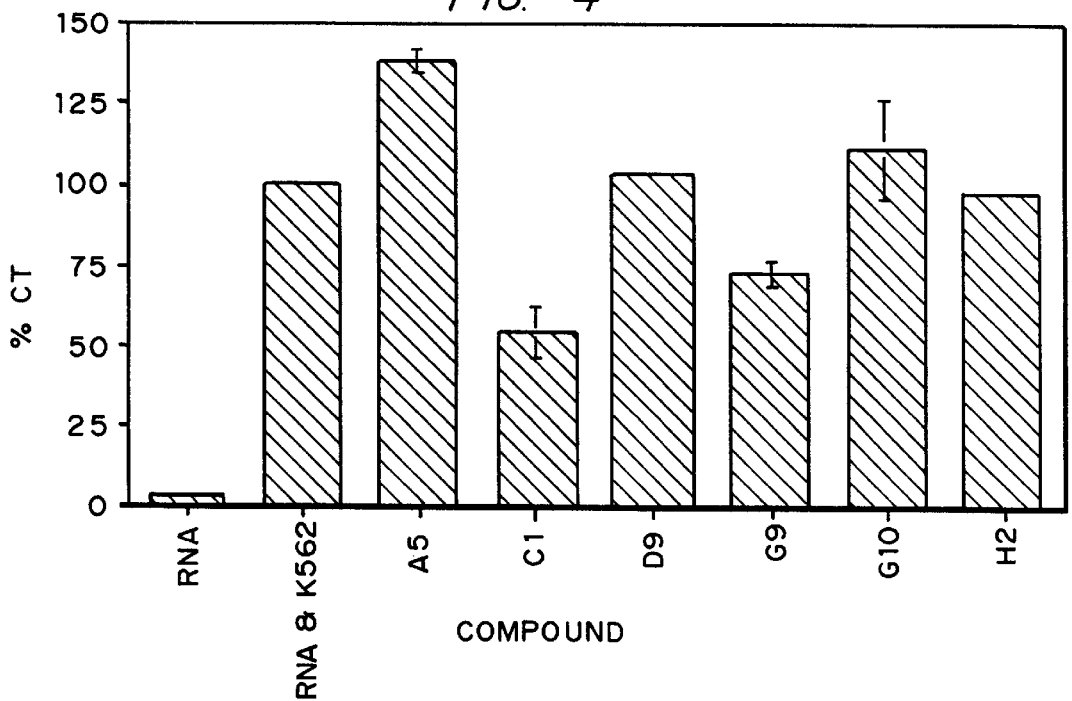

RNA SEQUENCES WHICH INTERACT WITH RNA-BINDING PROTEINS

CROSS-REFERENCE TO RELATED APPLICATIONS

This application is a continuation-in-part of U.S. application Ser. No. 08/690,010, filed Jul. 31, 1996.

BACKGROUND OF THE INVENTION

The invention is in the area of screening assays for identifying sequences involved in gene expression, and specifically for identifying binding sites for RNA binding proteins in RNA molecules.

The regulation of protein expression can occur at a number of levels: transcriptional, post-transcriptional, or post-translational. The modulation of protein expression is often critical for the treatment of disease. Recent work at modulating protein levels by altering transcriptional activity has resulted in preclinical research programs being established and licensing agreements being entered into. For example, Ligand Pharmaceuticals., Inc. (San Diego, Calif.) has entered into multiple drug discovery programs with large pharmaceutical companies based on their Signal Transducers and Activators of Transcription technology for use as anti-inflammatory, anti-cancer and hormone replacement therapies. In addition, Oncogene Science, Inc. (Uniondale, N.Y.) is using its proprietary gene transcriptional technologies to develop biopharmaceutical products for the treatment of cancer. Other companies, such as Signal Pharmaceuticals, Inc. (San Diego, Calif.) and Tularik, Inc. (San Francisco, Calif.) are developing small molecules that regulate transcription factors. While this approach holds promise, no compounds have yet to make it to clinical trials. The lack of specificity of transcription factors and requirement for nuclear localization are two concerns with this technology. In the first case, a drug affecting the binding of a transcription factor may affect transcription of many genes other than the target gene. In the second case, it is difficult to design a drug that both has the proper interaction with a targeted transcription factor and is transported into the nucleus where it exerts its effect. Inhibition of protein expression by targeting the RNA is an alternate approach involving antisense technology. The antisense technology has also generated much interest with several products in clinical trials (ISIS2105, ISIS2922 and ISIS2302). However, the major drawbacks with this approach are the cost of oligonucleotides, the ability to deliver the oligonucleotides into cells, and their inability to increase protein levels.

A major area of post-transcriptional regulation in eukaryotic cells involves the specific interaction of proteins with RNA. These RNA binding proteins (RBP) appear to mediate the processing of pre-mRNAs, the transport of mRNA from the nucleus to the cytoplasm, mRNA stabilization, the translational efficiency of mRNA, and the sequestration of some mRNAs. Recent studies have identified several RNA-binding motifs in a diversity of RBPs. The most common RNA binding protein motifs are the RNP motif, Arg-rich motif, RGG box, KH motif and double-stranded RNA-binding motif (for review see Burd and Dreyfuss, Science 265:615–621 (1994)). These motifs recognize both sequence and structure dependent RNA elements. In the case of the double-stranded RNA-binding motif, sequence recognition is unimportant. However, in addition to the double stranded structure, a positional effect for the double-stranded RNA may play a role in recognition (Bass, Nucleic Acids Symposium 33:13–15 (1995)) and some of these proteins may also require binding to Z-DNA prior to their activity on the doublestranded RNA (Herbert et al., Proc. Natl. Acad. Sci. USA 92:7550–7554 (1995)). In addition, other RNA binding proteins, such as AUBF (Malter, Science 246:664–666 (1989)) are likely to bind in a structure-independent manner.

Due to the clear importance of RNA/RBP interactions in the regulation of gene expression, these interactions would be an attractive target for drugs that affect them for modulation of protein levels in disease states. To fully exploit these interactions as therapeutic targets, however, requires a clear understanding of how these interactions affect expression, which RBPs are involved in the regulation of RNAs of interest, and the ability to study the modulating effects of potential drugs on the RNA/RBP interactions. To fully exploit such interactions also requires identification of binding sites for RBPs in RNA molecules of interest.

Many investigators have used mobility shift assays to detect RNA/protein interactions. However, the conditions established in one laboratory often fail to detect interactions of different molecules. In addition, the diversity of RNA structures and binding motifs in the protein have led numerous investigators to conclude that a single set of conditions would be impossible to define for detection of multiple different interactions. With more genes being identified as being post-transcriptionally regulated, a universal set of binding conditions would allow for the detection and characterization of the molecules involved in these interactions and ultimately would provide targets for which therapeutics could be developed. No such universal assay conditions have been previously described for the identification of RNA binding proteins, the RNA molecules and RNA-binding sites with which they interact, and the study of these interactions.

Due to the variety of RBPs and motifs it has generally been required that individual assay conditions be painstakingly worked out for each RNA/RBP combination, resulting in slow progress in studying known RBPs and their interactions and in slowed or prevented identification of additional RBPs and their RNA motifs. Clearly, some RNA/RBP interactions have gone undetected simply because the right assay conditions have never been tried. Thus, there is a need for more universal assay conditions which can be expected to detect the majority of specific RNA/RBP interactions. It would also be useful to have a method for identifying binding sites for RNA binding proteins in nucleic acid sequences since such binding sites are involved in the regulation of gene expression and can be expected to be valuable targets for the control or alteration of gene expression.

Therefore, it is an object of the invention to provide an assay for identifying binding sites for RNA binding proteins in nucleic acid sequences.

It is a further object of the invention to provide binding sites for RNA binding proteins.

It is a further object of the invention to provide an assay for the identification of compounds that affect the interaction of binding sites for RNA binding proteins.

It is a further object of the invention to provide a kit for identifying binding sites for RNA binding proteins in nucleic acid sequences.

It is a further object of the invention to provide nucleic acid sequences which interact with RNA binding proteins.

SUMMARY OF THE INVENTION

A major area of regulation of gene expression involves the regulatory effect of RNA binding proteins interacting with RNA molecules. Interactions between RNA molecules and RNA binding proteins are known to be involved in the following processes, modulation of which has the listed effect on encoded proteins.

RNA-stabilization→protein concentration
RNA destablization→protein concentration
Translational efficiency→protein concentration
RNA localization→protein concentration/function
RNA transcription→protein concentration (viral)
RNA editing→protein function
RNA splicing→protein function RNA binding protein binding sites can often be classified by the presence of certain structural motifs, sequence motifs, or both. RNA binding proteins can be similarly classified. Nearly every interaction between RNA molecules and RNA binding proteins can be detected using a single set of conditions. Assays employing the disclosed universal conditions are useful for identifying specific regions of an RNA molecule that interact with RNA binding proteins. Disclosed is a method for identifying possible binding sites for RNA binding proteins in nucleic acid sequences, and confirming the identity of such prospective binding sites by detection of interaction between the prospective binding site and RNA binding proteins. Also disclosed are specific binding sites of RNA binding proteins which have been identified using this method.

The disclosed method involves identification of possible binding sites for RNA binding proteins, by either searching databases for untranslated regions of gene sequences or cloning untranslated sequences using a single specific primer and a universal primer, followed by confirmation that the untranslated regions in fact interact with RNA binding proteins using the disclosed RNA/RBP detection assay. Genomic sequences can further be screened for putative binding site motifs in the nucleic acid sequences. Information about binding sites which are confirmed in the assay can also then be used to redefine or redirect the nucleic acid sequence search criteria, for example, by establishing or refining a consensus sequence for a given binding site motif.

It has been discovered that a single set of conditions can be used to detect nearly every interaction of RNA binding proteins and RNA molecules. Prior to this discovery it was thought that each specific interaction required separate optimized conditions in order to be detected. Assays employing the disclosed universal conditions are useful for identifying specific regions of an RNA molecule that interact with RNA binding proteins. This identification assay can be modified to include identification of compounds that modulate the interaction of an RNA binding protein with an identified binding site.

BRIEF DESCRIPTION OF THE DRAWINGS

FIG. 3 is a graph of the amount of radioactively labeled RNA retained on a filter (expressed in percent of the amount of RNA retained on a filter in a reference binding solution) following loading of various binding solutions. All of the binding solutions contained radioactively labeled IRE RNA either alone or including various other components. The first column represents a binding solution without RNA binding protein. The remaining columns represent binding solution containing RNA binding protein (K562 extract). Hemin indicates that the binding solution included the indicated amount of hemin as a test compound. Des indicates that the binding solution included the indicated amount of desferroxiamine as a test compound.

FIG. 4 is a graph of the amount of radioactively labeled RNA retained on a filter (expressed in percent of the amount of RNA retained on a filter in a reference binding solution) following loading of various binding solutions. All of the binding solutions contained radioactively labeled AUUUA RNA either alone or including various other components. The first column represents a binding solution without RNA binding protein. The remaining columns represent binding solution containing RNA binding protein (K562 extract). Columns 3 through 8 correspond to binding solutions including the indicated test compound.

DETAILED DESCRIPTION OF THE INVENTION

Figure 1:
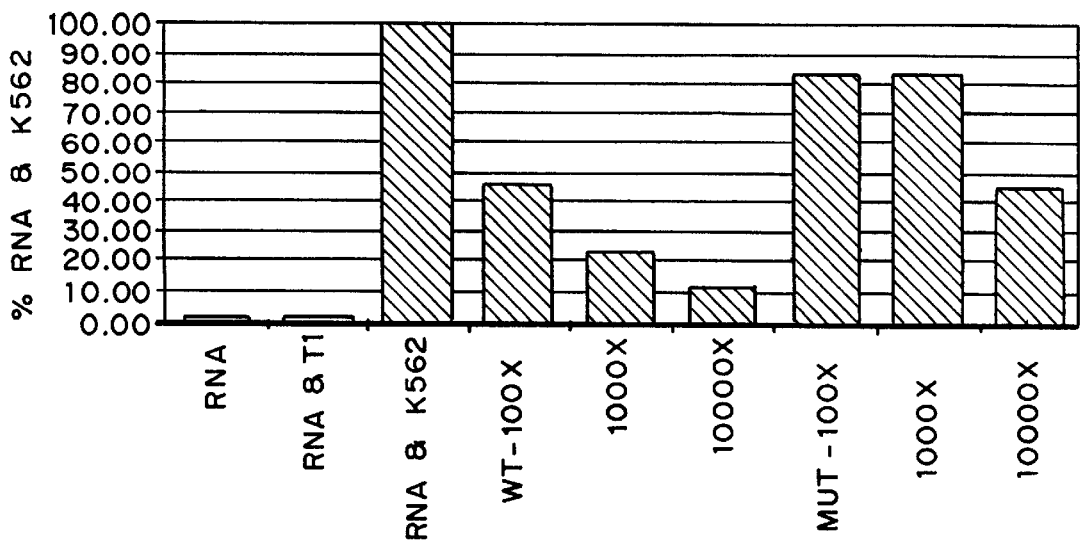
FIG. 1 is a graph of the amount of radioactively labeled RNA (in counts per minute) retained on a filter following loading of various binding solutions. All of the binding solutions contained radioactively labeled APP RNA either alone or including various other components. T1 indicates that the binding solution was treated with RNAse T1 prior to loading. The first two columns represent binding solutions without RNA binding protein. The remaining columns represent binding solution containing RNA binding protein. WT indicates that the binding solution included the indicated amount of unlabeled wild type RNA as a competitor. MUT indicates that the binding solution included the indicated amount of unlabeled mutant RNA as a competitor.

Disclosed is a method for identifying possible binding sites for RNA binding proteins in nucleic acid sequences, and confirming the identity of such prospective binding sites by detection of interaction between the prospective binding site and RNA binding proteins. For use in this method, also disclosed are universal conditions and procedures that can be applied to any RNA molecule and any RNA binding protein to detect interactions between them. The basic detection procedure can be adapted to detect interactions between RNA binding proteins and RNA molecules in bulk, interactions between RNA binding proteins and a specific RNA molecule, and interactions between RNA molecules and a specific RNA binding protein. The detection procedure can thus be used to, for example, detect all of the RNA binding proteins present in a sample, such as a cell or tissue extract, with a specific RNA molecule, such as the transcript from a gene of interest. Similarly, the detection procedure can be used to detect all of the RNA molecules present in a sample, such as a cell or tissue extract, with a specific RNA binding protein.

The detection procedure, and a kit therefor, is useful as a research tool, both for identifying interactions between RNA molecules and RNA binding proteins, and for identifying compounds that modulate such interactions. Compounds identified in such a screening assay could be useful for regulating the expression of RNA molecules of interest The importance of interactions between RNA molecules and RNA binding proteins was described above. All of the uses can be accomplished by applying the basic detection procedure and specific adaptions of the basic detection procedure as described herein.

It has been discovered that a single set of conditions can be used to detect nearly every interaction of RNA binding proteins and RNA molecules. These conditions allow detectable complexes between RNA binding proteins and RNA molecules and are thought to mimic physiological conditions in cells where such interactions normally occur. Prior to this discovery it was thought that each specific interaction required separate optimized conditions in order to be detected.

As used herein, interactions between RNA binding proteins and RNA molecules which are referred to as "possible" are intended to mean those interactions which are specific and which occur under at least one set of conditions (e.g. in vivo or optimized binding assay conditions). In the context of the disclosed universal method of detecting interactions between RNA binding proteins and RNA molecules, the method will detect a majority of the interactions between RNA binding proteins and RNA molecules which are possible. The meaning of the term "specific interaction" is generally understood to mean interactions that are based on specific characteristics of the interacting molecules and not on general characteristics. For example, certain RNA binding proteins recognize and bind specifically to sites in RNA molecules having the nucleotide sequence AUUUA. This is a specific interaction. Conversely, some proteins bind RNA molecules in general (i.e. non-specifically) based on the general chemical characteristics of all RNA molecules. In general, an interaction can be identified as a non-specific interaction by determining that the interaction can be prevented in the presence of a non-specific competitor.

I. Components

A. Binding Solution

Interactions between RNA binding proteins and RNA molecules are facilitated in a binding solution. The binding solution contains one or more RNA molecules and buffer components. The buffer components include a buffer, a monovalent cation, a divalent cation, a reducing agent, and a density agent. It is preferred that the buffer is Bis-Tris Propane at a pH of about 8.5 and at a concentration of about 7.5 mM, the monovalent cation is $K^+$ at a concentration of about 50 mM, the divalent cation is $Mg^{++}$ at a concentration of about 1 mM, the reducing agent is dithiotlireitol at a concentration of about 0.2 mM, and the density agent is glycerol at a concentration of about 10 percent (v/v).

These conditions have been optimized to be universally applicable. It is most preferred that the optimum conditions be used. However, one, or less preferably two, of the buffer components can be varied in the manner disclosed below. For varying certain buffer components, it is preferred that (1) the buffer is HEPES, Tris, or Bis-Tris Propane, each at a pH between about 8 and 10 and at a concentration of between about 5 and about 100 mM, (2) the monovalent cation is $K^+$, $Na^+$, or $NH_4^+$, each at a concentration of between 0 and about 100 mM, (3) the divalent cation is $Mg^{++}$, $Ca^{++}$, or $Fe^{++}$, each at a concentration of between 0 and about 5 mid, (4) the reducing agent is dithiothreitol or $\beta$-mercaptoethanol, at a concentration of between 0 and about 1 mM, and the density agent is glycerol or polyethylene glycol at a concentration of between 0 and about 20 percent (v/v).

For most RNA molecules, the reducing agent does not appear to be critical, although there is a trend to slightly better binding in the presence of a reducing agent, preferably DTT. However, in some cases the reducing agent makes a significant difference in the detection of interactions. Accordingly, the use of a reducing agent is preferred. A density agent does not appear to be required for detecting the interaction between RNA molecules and RNA binding proteins. However, when interactions are analyzed by gel mobility shift, the presence of a density agent does enhance the quality of the bands. Accordingly, the use of a density agent is preferred.

The binding solution can include other components that aid in the formation of specific interactions. For example, a competitor of non-specific RNA/protein interactions can be added to reduce the background of nonspecific interactions. Poly r(G), tRNA, and heparin, are preferred competitors of non-specific RNA/protein interactions.

It is intended that a concentration range stated as between 0 and about a specific concentration does not encompass a concentration of zero but does encompass the specific concentration and concentrations up to about 10% greater than the specific concentration. It is also intended that a concentration range stated as between about a first specific concentration and about a second specific concentration encompasses the first specific concentration, concentrations up to about 10% lower than the first specific concentration, concentrations between the first and second specific concentrations, the second specific concentration, and concentrations up to about 10% greater than the second specific concentration. It is intended that a concentration range stated as from a first specific concentration to a second specific concentration encompasses the first specific concentration, concentrations between the first and second specific concentrations, and the second specific concentration. It is also intended that a concentration range stated as from 0 to a specific concentration encompasses a concentration of zero, concentrations between zero and the specific concentration, and the specific concentration.

Unless otherwise noted, all concentrations of buffer components are intended to be the final concentration of these components in a completely formed binding solution. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA.

It is preferred that the concentration of extraneous compounds be kept to a minimum in binding solutions. It is understood, however, that samples of RNA binding proteins and RNA molecules may contain additional compounds.

The concentration in the binding solution of such compounds can be reduced by, for example, diluting the sample to the greatest extent possible when forming the binding solution.

B. RNA Binding Proteins

RNA binding proteins for use in the disclosed method can be part of a crude cellular or nuclear extract, partially purified, or extensively purified. RNA binding proteins can be used either in isolation or in combination one or more other RNA binding proteins. When the goal is to identify RNA binding proteins in a sample, it is preferred that the sample be an unpurified or partially purified extract so that the largest variety of RNA binding proteins will be present. When the goal is to identify RNA molecules, or portions of an RNA molecule, that interact with a specific RNA binding protein, it is preferred that the RNA binding protein be substantially purified. For identification of RNA binding protein binding sites which have relevance to particular conditions, disease states, developmental stage, or cell types, it is preferred that RNA binding proteins be obtained from the cells of interest or cells from subjects exhibiting the particular condition or disease state.

RNA binding proteins can be prepared using known methods for preparing cellular extracts and for purifying proteins. Methods for preparing extracts containing RNA binding proteins and for purifying known RNA binding proteins are described in, for example, Ashley et al., *Science* 262:563–566 (1993), Rouault et al., *Proc. Natl. Acad. Sci. USA* 86:5768–5772 (1989), Neupert et al., Nucleic Acids Research 18:51–55 (1990), Zhang et al., *Molecular and Cellular Biology* 13:7652–7665 (1993), and references cited in Burd and Dreyfuss, *Science* 265:615–621 (1994). Individual RNA binding proteins can also be produced recombinantly using known techniques. DNA encoding RNA binding proteins can be obtained from known clones, by synthesizing a DNA molecule encoding an RNA binding protein with a known amino acid sequence, or by cloning the gene encoding the RNA binding protein. Techniques for recombinant expression of proteins and methods for cloning genes encoding known proteins are described by, for example, Sambrook et al., *Molecular Cloning* (Cold Spring Harbor Laboratory, 1989).

Detection of interactions between RNA binding proteins and RNA molecules can be facilitated by attaching a detectable label to the RNA binding protein. Generally, labels known to be useful for proteins can be used to label RNA binding proteins. Preferred labels for RNA binding proteins are $^{125}I$, $^3H$, and $^{35}S$. When the RNA binding protein is made recombinantly, it can be labeled by incorporation of labeled amino acids. Techniques for labeling and detecting labeled proteins are well known and are described in, for example, Sambrook et al., and Ausubel et al., *Current Protocols in Molecular Biology* (John Wiley & Sons, Inc., 1996). Detection of RNA binding proteins can also be accomplished with antibodies specific for the RNA binding protein. The production and use of antibodies for this purpose is well known and is described in, for example, Johnstone and Thorpe, *Immunochemistry in Practice* (Blackwell Scientific Publications, 1987).

C. RNA Binding Protein Binding Sites

In order to search nucleic acid sequences for putative RNA binding protein binding sites, criteria for such identification are required. Some binding site motifs are known and provide a basis for establishing search criteria for related binding sites. Such motifs also serve as a model for the establishment of criteria for any new binding sites or binding site motifs which are identified. It is known that RNA binding proteins interact with RNA molecules based on, for example, nucleotide sequence alone, structures formed by RNA molecules, and combinations of sequence and structure. It is understood, of course, that structural motifs of binding sites are based on the nucleotide sequence of the RNA molecules. However, it is also understood that RNA molecules which support formation of specific structures are not usually limited to any specific sequences. An example of this are RNA molecules which form double stranded structures. In such cases, the most significant determinant for formation of the structure is the presence of regions in the RNA molecules which are complementary.

Several motifs for RNA binding protein binding sites are known. These include motifs which can be identified as AUUUA, histone, IRE, U1, APP, and RRE. These motifs are known to interact with certain RNA binding protein motifs such as double-stranded RNA binding motifs (IRE), RGG box (APP), Arg-rich motifs (RRE), and RNP motifs (U1).

However, these motifs are represented by short sequences within a structure, thus limiting the effectiveness of searching the database by sequence identity. Since most motifs are found in the untranslated regions of mRNAs, known untranslated regions can be analyzed for their ability to interact specifically with an RNA binding protein. In addition, methods are known, such as RACE, and are described, for example, poly(A) PCR, for identification of new untranslated sequences. Finally, a search of DNA databases for known motifs followed by structural analysis of the adjacent sequences can be used to clone sequences containing previously identified motifs. Preferably, such a search is conducted using digitally stored (that is, computer-based) sequence information and computer search algorithms.

D. RNA Molecules

RNA molecules for use in the disclosed method can be part of a crude cellular or nuclear extract, partially purified, or extensively purified. RNA molecules can also be made by in vitro transcription or by direct synthesis. RNA molecules can be used either in isolation or in combination with one or more other RNA molecules. When the goal is to identify RNA molecules in a sample, it is preferred that the sample be an unpurified or partially purified extract so that the largest variety of RNA molecules will be present. When the goal is to identify RNA binding proteins that interact with a specific RNA molecule, it is preferred that the RNA molecules be substantially purified. For this purpose, it is most preferred that the RNA molecule be produced in vitro.

RNA molecules can be prepared using known methods for preparing cellular extracts and for purifying RNA. Methods for preparing extracts containing RNA molecules are described in, for example, Sambrook et al., and Ausubel et al. Individual RNA molecules can also be produced recombinantly using known techniques, by in vitro transcription, and by direct synthesis. For recombinant and in vitro transcription, DNA encoding RNA molecules can be obtained from known clones, by synthesizing a DNA molecule encoding an RNA molecule, or by cloning the gene encoding the RNA molecule. Techniques for in vitro transcription of RNA molecules and methods for cloning genes encoding known RNA molecules are described by, for example, Sambrook et al.

Detection of interactions between RNA binding proteins and RNA molecules can be facilitated by attaching a detectable label to the RNA molecule. Generally, labels known to be useful for nucleic acids can be used to label RNA molecules. Examples of suitable labels include radioactive isotopes such as $^{33}P$, $^{32}P$, and $^{35}S$, fluorescent labels such as fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, and biotin.

Labeled nucleotides are the preferred form of label since they can be directly incorporated into the RNA molecules during synthesis. Examples of detection labels that can be incorporated into amplified RNA include nucleotide analogs such as BrdUrd (Hoy and Schimke, Mutation Research 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.* 22:3226–3232 (1994)).

A preferred nucleotide analog label for RNA molecules is Biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into RNA molecules, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.).

E. Identified RNA Binding Protein Binding Sites.

Nucleic acid segments identified as having RNA binding protein binding sites can be used for several purposes. As described elsewhere herein, the nucleotide sequence or structure of such nucleic: acid segments can be used to determine the consensus sequence and/or structure binding site motifs. An RNA molecule including the nucleotide sequence of the identified nucleic acid segment can be used in an assay to identify compounds modulating the interaction of the RNA molecule and RNA binding proteins. The identified segment can also be incorporated into a recombinant construct such that expression of the construct is controlled by the nucleic acid segment. For example, an untranslated region of an mRNA identified as interacting with an RNA binding protein can be used as all or a part of the untranslated region of a heterologous RNA. It is expected that such recombinant RNA molecules will interact with the cognate RNA binding protein of the heterologous untranslated region and expression of the RNA will be affected by this interaction. This is analogous to recombining promoters with heterologous coding regions to alter or control the expression of the coding region. It is preferred that recombinant constructs including RNA binding protein binding sites be included in expression vectors such that a recombinant RNA transcript can be produced which includes RBP binding site and heterologous sequences. An identified RBP binding site is said to be operatively linked to heterologous sequences when in an RNA molecule including both binding site and the heterologous sequences, or in a construct in which an RNA transcript can be made including both binding site and the heterologous sequences. As used herein, heterologous sequences are nucleotide sequences that are not naturally associated in the same nucleotide molecule with a reference sequence such as an RBP binding site.

Four nucleic acid segments having RNA binding protein binding sites have been identified and confirmed using procedures described herein. Each of the segments represent the 5' untranslated region (UTR) of mammalian mRNA. One (SEQ ID NO:1) is the UTR of rat glucose transporter mRNA (Glut1). The identified segment is a portion of the sequence at GenBank accession number M13979. The initiation codon begins at position 209 of SEQ ID NO:1. Another identified segment (SEQ ID NO:2) is the 5' UTR of human 3-hydroxy-3-methyl-glutaryl CoA reductase (HMG,CoA Red). The identified segment is a portion of the sequence at GenBank accession number M15959. The initiation codon begins at position 106 of SEQ ID NO:2. Another identified segment (SEQ ID NO:3) is the 5' UTR of human C4b-binding protein alpha chain. The identified segment is a portion of GenBank accession number M62448. Another identified segment (SEQ ID NO:4) is the 5' UTR of human CD45. The identified segment is a portion of GenBank accession numbers M23461 and M23499.

As used herein, a nucleic acid molecule or nucleic acid segment referred to as having a nucleotide sequence is intended to mean a nucleic acid molecule or segment having the nucleotide base sequence referred to in any of its corresponding forms. For example, in the case of an RNA nucleotide sequence (such as SEQ ID NOs:1–4), it is specifically intended, unless otherwise indicated, that nucleotide molecules or segments referred to as having such an RNA nucleotide sequence include, for example, nucleotide molecules or segments having the corresponding DNA nucleotide sequence (where T is substituted for U). Similarly, in the case of a DNA nucleotide sequence, it is specifically intended, unless otherwise indicated, that nucleotide molecules or segments referred to as having such a DNA nucleotide sequence include, for example, nucleotide molecules or segments having the corresponding RNA nucleotide sequence (where U is substituted for T).

II. Method

The basic method for identifying binding sites for RNA binding protein in nucleic acid sequences involves searching nucleic acid sequences for complete untranslated regions (UTRs) from known mRNAs. The 5' UTRs can be identified as complete based on information associated with the sequence, such as designation of a +1 site being the start of the primary transcript, identification of a TATA box in the genomic sequence and search of a guanidine nucleotide approximately 30 nucleotides 3' to the TATA box, or through literature searches for identification of transcript size from which the size of the UTR can be inferred. The 3' UTRs can be identified as complete based on the identification of poly(A) stretch at the 3' end of the sequence, a polyadenylation signal approximately 30 nucleotides from the 3' end of the sequence or through published literature. As defined above, selection criteria for these UTRs has been established such that once the full-length or near full-length UTRs are identified from an appropriate DNA database, the UTRs can be synthesized or isolated from an appropriate tissue or cell. For example, using the identified UTR sequences, primers can be designed for use in PCR, where the UTRs are synthesized by PCR of RNA from the appropriate tissue or cell. Once the UTRs are synthesized, the presence of binding sites can be determined using the disclosed detection assay. In the absence of full-length UTRs, the UTR can be cloned by well-established methods such as RACE, for the cloning of 5' UTRs, or poly(A) PCR for the cloning of 3' UTRs.

A further application of this method is the identification of binding sites related to known binding sites for RNA binding proteins in nucleic acids sequences, involving searching nucleic acids sequences based on similarity to the sequence and/or structure of previously identified sites. Once established, such criteria can be used to identify putative RNA binding protein binding sites in nucleic acids sequences. Thus, another purpose or use of the disclosed method is to identify new RNA binding protein binding site motifs and establish criteria for a nucleic acid search operation.

The nucleic acid sequences to be searched can be either known sequences (for example, sequences available in sequence databases) or sequences obtained by nucleic acid sequencing of any nucleic acid molecules of interest. Although it is preferred that the nucleic acid sequences to be searched are identified as, or known to be, represented in RNA molecules in a cell, such knowledge is not required. In fact, a search of nucleic acid sequences in general, such as genomic sequences, may be used to identify a sequence containing an untranslated region as one that may be transcribed.

One preferred mode for the disclosed method, which is a binding site identification mode, involves a search of known nucleic acid sequences for putative binding sites based on sequence criteria (which may reflect a full-length UTR, or recognition sequence and/or the potential to form a characteristic structure). Putative binding sites are then embodied in RNA by either cloning or direct synthesis, and testing for interaction between the putative binding sites and RNA binding proteins. RNA molecules containing confirmed sites can then be used in a screening assay to identify compounds which modulate the interaction of RNA binding proteins with the RNA molecules. Finally, identified compounds can be tested for an effect on expression of a corresponding RNA molecule in a cell. It is preferred that this binding site identification mode be specifically directed to a search of nucleic acid sequences of genes known or suspected of being involved in disease conditions.

Another preferred mode for the disclosed method, which is a criteria establishing mode, involves screening RNA molecules for interactions between the RNA molecules and RNA binding proteins. The specific binding sites in the RNA molecules can then be identified by assaying interactions between RNA binding proteins and RNA molecules representing subfragments of RNA molecules identified as interacting with RNA binding proteins. The nucleic acid sequence of identified sites can be determined and used to establish criteria for future sequence-based binding site identifications. If a group of related binding sites are identified, for example, by interaction with a common RNA binding protein, a consensus or binding site motif can be established. This information can be used to extend or refine the nucleic acid sequence search criteria. The established search criteria can then be used to identify RNA binding protein binding sites in nucleic acid sequences using, for example, a binding site identification mode of the disclosed method. It is contemplated that consensus features of binding sites identified in a group of related RNA molecules (for example, RNA molecules which are, or are expected to be, coordinately expressed) will identify binding sites which are preferred targets for compounds affecting the interaction of the binding site and the RNA binding protein.

Another preferred mode for the disclosed method, which is a binding site identification mode, involves screening RNA molecules for interactions between the RNA molecules and RNA binding proteins. The specific binding sites in the RNA molecules can then be identified by assaying interactions between RNA binding proteins and RNA molecules representing subfragments of RNA molecules identified as interacting with RNA binding proteins. Identified sites can then be used in a screening assay to identify compounds which modulate the interaction of RNA binding proteins with the RNA molecules. Finally, identified compounds can be tested for an effect on expression of a corresponding RNA molecule in a cell. It is preferred that this binding site identification mode be specifically directed to a search of nucleic acid sequences of genes known or suspected of being involved in disease conditions.

A. Nucleic Acid Sequence Searching

Nucleic acid sequence searching as part of a search operation involves a search of nucleic acid sequences for the presence of sequences having certain characteristics. Suitable characteristics, or the determination of suitable characteristics are disclosed elsewhere herein. In general, for the purposes of searching nucleic acid sequences, such characteristics include the full-length 5' or 3' untranslated regions within the mRNA or specific RNA binding protein binding sites which are preferably expressed in terms of a nucleotide sequence or sequences. Such nucleotide sequences can include, for example, a specific nucleotide sequence, a consensus or generic sequence, and groups of sequences in combination (including combinations having specific relationships). As used herein, nucleic acid sequence and nucleotide sequence are both considered to refer to the linear arrangement nucleotide residues within a nucleic acid molecule.

Nucleic acid sequence searching can be performed using any suitable means of analyzing or searching nucleotide sequences. Techniques of searching for nucleotide sequences of interest within a larger nucleotide sequence or group of nucleotide sequences are well established. A group of nucleotide sequences to be searched is generally referred to herein as a sequence database, or nucleotide sequence database. Preferred techniques make use of digitally stored (that is, computer-based) nucleotide sequences and involve computer-based searching. Preferred nucleotide sequence databases for use with the disclosed method are the large computer databases such as GenBank and EMBL. Other preferred nucleotide sequence databases include compilations of cDNA sequences, including compilations of expressed sequence tag (EST) sequences, both those in the public domain, for example the Washington University/ Merck collaboration on identification of expressed sequence tags (ESTs), and those developed privately, for example, the EST and sequence database established by Human Genome Sciences, Inc. and subsequently licensed to Smith Klein and others. In addition, the specific databases being established by genomic companies such as GeneLogic and Aeiveos, represent sources of sequences presumably related to specific disease states. It is also contemplated that nucleotide sequence information in any form can be subjected to a search. For example, searches can be made for patterns of bands on a sequence gel, or for data patterns representative of nucleotide sequences present in, for example, the data output of solid-state sequenators, automated chromatographic sequenators, sequencing gel scanners, and hybridization-based sequencing techniques.

Many computer programs are known and available for searching nucleotide sequences. Most computer sequence databases include such programs for use with the database. Preferred computer programs for nucleotide sequence searches are Blast, GCG FASTA, and Genworks DNA query. It is contemplated that the specific operating systems, search programs, and organization of nucleotide sequence databases will continue to be altered and updated in the future. However, since a primary and continuing purpose of such programs and databases will be searching and comparison of nucleotide sequences, such changes are not expected to prevent their use in the disclosed method. It is understood that nucleic acid sequence searching for the disclosed method can be performed using any suitable method including visual inspection of printed or written sequences, and does not rely on any specific searching technology.

B. Detection Of RNA/RBP Interactions

The confirmation operation, that is, direct determination of an interaction between an RNA binding protein and a putative binding site, can be performed using the disclosed assay. This assay can also be used to screen for binding sites in RNA molecules. The basic method for detecting interactions between RNA molecules and RNA binding proteins involves forming a binding solution containing the RNA molecules and 1× binding buffer, heating the binding solution to denature the RNA molecules, cooling the binding solution to the reaction temperature, adding the RNA binding proteins to the binding solution, and detecting the interactions between the RNA molecules and the RNA binding proteins.

1. Forming the Binding Solution

The binding solution contains one or more RNA molecules, buffer components, and non-specific competitors. The buffer components include a buffer, a monovalent cation, a divalent cation, a reducing agent, and a density agent. The binding solution is formed by combining and/or mixing together the constituents of the binding solution in any manner that results in a binding solution having the required composition. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA. Thus, the manner in which the final composition of the binding solution is arrived at is not critical. It is intended that any combination of solutions and components that achieves this result is encompassed by this step.

2. Heating and Cooling the Binding Solution

The formed binding solution is heated and cooled in 1× binding buffer in order to denature any higher order structure in the RNA molecules. Such structures can make the RNA molecules less accessible to the RNA binding proteins. When using RNA molecules purified from natural sources, it is also possible that other molecules can remain bound to the RNA. The heating step can serve to release such molecules. The heating and cooling step involves subjecting the binding solution to a heat source until it reaches a sufficient temperature, and then allowing the solution to cool to the reaction temperature. The temperature to which the binding solution is heated can be any temperature that will substantially denature the RNA molecules present in the binding solution. It is understood that different temperatures will be sufficient for different RNA molecules. For example, shorter RNA molecules and RNA molecules with a low GC content will, in general, be substantially denatured at lower temperatures. However, it is preferred that a single temperature be used for the heating step. In this case, it is preferred that a temperature sufficient to substantially denature RNA molecules in general be used. A preferred temperature is 85° C. After allowing the solution to cool to the reaction temperature, the RNA binding protein is added to the binding solution prior to incubation at the appropriate temperature for RNA-protein binding, preferably 37° C.

3. Detecting Interactions

Interactions between RNA binding proteins and RNA molecules can be detected using any suitable procedure. It is preferred that detection involve separation of interacting RNA molecules and RNA, binding proteins. This can be accomplished, for example, by separating components in the binding solution on the basis of size or physical properties. Two preferred methods of separation and detection of interacting RNA molecules and RNA binding proteins are filter binding and gel mobility shift.

a. Filter binding. Filter binding involves trapping interacting molecules on a filter while non interacting molecules pass through the filter. This procedure is known to those of skill in the art. For example, prewet nitrocellulose filters are equilibrated in 1× binding buffer. The binding reaction is then applied to the filter by vacuum filtration to remove unbound RNA. The filter is washed in 1× binding buffer, scintillation cocktail is added and the amount of protein-bound RNA is determined by scintillation counting.

For assays involving filter binding, it is also preferred that a non-interacting control assay be performed. Such a control is used to determine the detectable signal retained in the absence of specific RNA/RNA binding protein interaction. Preferably, such a non-interacting control assay is performed by substituting a mutant RNA molecule—one that does not interact specifically with the RNA binding protein—for the RNA molecule used in corresponding binding assays. The level of detectable signal bound to the filter in the non-interacting control indicates the contribution of background, or non-specific, signal present in the level of detectable signal measured for the binding assays. In the high throughput screening assay, the non-interacting control is also a control for the control assays (that is, assays not containing a test compound). It is expected that the level of background signal can be reduced by including a low concentration of detergent in the wash buffer. Preferred detergents for this purpose are Tween 20 and Triton N-101. For a given set of test reactions, a non-interacting control assay can be used to determine the effectiveness of the washes.

It is preferred that the concentration of RNA binding protein in the disclosed assays be at least 0.5 $\mu g/\mu l$ or between 0.5 $\mu g/\mu l$ and 1.0 $\mu g/\mu l$. For assays using filter binding, the filter is preferably either pure nitrocellulose or a mixed cellulose ester (MCA). For the disclosed assay, the mixed cellulose ester filters bound more counts than pure nitrocellulose. For the filters, a 0.2 $\mu m$ pore size (8000 dalton MW cutoff) is most preferred, although MCA filter plates with a 0.45 $\mu m$ pore size (20,000 dalton MW cutoff) are also preferred. The lower molecular weight cutoff allows detection of binding interactions between RNA and small molecular weight proteins. For the high throughput screening assay, it is preferred that the binding reactions are carried out in 96 well v-bottom plates in a final volume of 10 $\mu l$. For this, the samples are loaded onto a 96 well Millipore filter plate.

For assays using filter binding, it is preferred that, following incubation and prior to loading unto the filter, the reactions be brought to a larger final volume, most preferably a final volume of 110 μl, by the addition of a solution, referred to as the dilution solution. Preferred dilution solutions include 1× Bis-Tris propane (BTP) binding buffer with glycerol, 1× BTP without glycerol, TE, phosphate buffered saline (PBS), and trichloroacetic acid (TCA), with 1× BTP without glycerol being most preferred. It is most preferred that the dilution solution have the same buffer components (preferably at the same final concentration) as used in the binding solution except lacking the density agent. This dilution allows more even loading of the sample on the filter plate. It is contemplated that the preferred final volume used should differ depending on the area of filter to which the assay solution will be applied. Thus, assays in which larger filter areas are used are preferably brought to a final volume greater than 110 μl and assays in which smaller filter areas are used are preferably brought to a final volume less than 110 μl.

It is preferred that the assay solution be loaded onto the filter under vacuum. After loading, it is preferred that the filters be washed, preferably two times. Preferred wash buffers (also referred to as the wash solution) include 1× BTP binding buffer with glycerol, 1× BTP without glycerol, TE, PBS, and TCA, with 1× BTP without glycerol being most preferred. It is most preferred that the wash buffer have the same buffer components (preferably at the same final concentration) as used in the binding solution except lacking the density agent. It is also preferred that the wash buffer be cold (that is, below room temperature).

b. Gel mobility shift. Gel mobility shift involves resolving interacting and non-interacting RNA molecules and RNA binding proteins on a gel by electrophoresis and visualizing the location and amount of components that migrate to different extents. Interacting RNA molecules and RNA binding proteins tend to migrate less in the gel than non-interacting molecules by virtue of their greater mass. Gel mobility shift assays can be performed as follows. After incubation of the binding reaction, 6× loading buffer (30% glycerol, 0.25% xylene cyanol, 0.25% bromophenol blue) is added to a final concentration of 1×. The reaction is then loaded into the wells of a polyacrylamide gel (generally 4 to 8%) prepared in Tris-borate EDTA (TBE) buffer (90 mM Tris-borate, 2 mM EDTA, pH 8). The protein-bound RNA is separated from the unbound RNA by applying a constant voltage (150 to 175 V) to the gel and allowing the gel to run until the bromophenol blue has reached the bottom of the gel. The gel is the dried in vacuo at 80° C. The unbound RNA and the protein-bound RNA are then visualized autoradiographically. In cases where it is desirable to know the molecular weight of the RNA-protein complex, the binding reaction is subjected to ultraviolet light to covalently crosslink the complex. 6× loading buffer (3.75M Tris, 30% βME, 13.8% sodium dodecyl sulfate (SDS), 30% glycerol, pH 6.8) is added to the crosslinked reaction at a final concentration of 1× and the mixture is loaded onto a SDS-polyacrylamide gel (generally 8 to 12%). The gel is run in a Tris-glycine buffer (25 mM Tris, 192 mM glycine, 0.1% SDS) at 30 mA until the molecular weight markers are adequately separated. The gel is dried and the RNA-protein complex visualized autoradiographically.

c. Ribonuclease digestion. For some assays it may be desirable to eliminate those RNA molecules, or those regions of an RNA molecule, that are not involved in an interaction with RNA binding proteins. For example, when a large RNA molecule is used in the assay, binding of an RNA binding protein might result in an RNA/protein complex only slightly larger than the RNA molecule alone. When detecting such a complex by gel mobility shift, the resulting shift may not be easily detectable. When detecting such a complex by filter binding, the RNA molecule alone may be sufficiently large to be retained by the filter. Such potential problems can be mitigated by digesting RNA not involved in interactions. This is easily accomplished by subjecting the binding solution to ribonuclease digestion. Only the unbound or non-interacting RNA will be digested. The regions of RNA bound by RNA binding proteins will be protected from digestion by the protein.

4. Identifying RNA Molecules and RNA Binding Molecules That Interact With Specific RNA Binding Proteins and RNA Molecules Identification of RNA molecules that interact with a specific RNA binding protein can be accomplished by forming a binding solution comprising one or more RNA molecules, and buffer components comprising a buffer, a monovalent cation, a divalent cation, a reducing agent, and a density agent, adding the specific RNA binding protein, and detecting interactions between the one or more RNA molecules and the RNA binding protein. Those RNA molecules that interact can be identified by specific sequence analysis. An assay of this type can be used to identify all those RNA molecules in a given sample which are specific for an RNA binding protein of interest. The identification of such RNA molecules can lead to the identification of genes encoding RNA molecules regulated by the RNA binding molecules of interest.

In a similar way, RNA binding proteins that interact with a specific RNA molecule can be identified by forming a binding solution comprising the RNA molecule of interest, and the buffer components, adding one or more RNA binding proteins, and detecting interactions between the one or more RNA binding proteins and the RNA molecule.

5. Identifying Genes Encoding RNA Molecules That Interact With RNA Binding Proteins The genes encoding RNA molecules that interact with RNA binding proteins can be identified by synthesizing a labeled cDNA from the RNA molecule and using the cDNA to screen a library of genes thought to contain the gene encoding the RNA molecule. The gene encoding the RNA molecule can then be identified by sequence analysis. The identity of the gene can be confirmed by determining the intron-exon structure of the gene, cloning the exons into a vector and transcribing the RNA in vitro. The in vitro transcribed RNA can then be used to form a binding solution, and the interactions with the RNA binding proteins can be detected and compared with the interactions of the original RNA and RNA binding protein. The gene is confirmed as encoding the RNA molecule if the interactions between the test RNA and the RNA binding proteins are substantially the same as those of the original RNA and the RNA binding proteins. Procedures for all of these manipulations are well established and known to those of skill in the art and/or are described herein.

6. Identifying Genes Encoding RNA binding Proteins

The genes encoding RNA binding proteins that interact with RNA molecules can be identified by isolating the binding protein and determining a portion of the amino acid sequence. This sequence can then be used to generate peptides which in turn can be used to produce antibodies to the RNA binding protein. Additionally, or alternatively, the peptide sequence can be reverse translated to generate a cDNA probe. The probes or antibodies can then be used to screen a cDNA library (expression library when antibodies are used) and resulting cDNA clones used to screen a genomic library. The gene encoding the RNA binding protein can then be identified by sequence analysis. The identity of the gene can be confirmed by determining the intron-exon structure of the gene, cloning the exons into a vector and performing in vitro transcription/translation to express the protein or by expressing the protein in vivo. The expressed protein can then be added to the binding solution, the interactions with the RNA molecules detected and compared with the interactions of the original RNA binding protein and RNA molecules. The gene is confirmed as encoding the RNA binding protein if the interactions between the test protein and the RNA molecules and the original protein and RNA molecules are substantially the same. Procedures for all of these manipulations are well established and known to those of skill in the art and/or are described herein.

7. Identifying Regions In RNA Molecules That Interact With RNA Binding Proteins Regions in RNA molecules that interact with RNA binding proteins can be identified by forming a binding solution comprising (1) an RNA molecule from a subset of RNA molecules consisting of successively smaller fragments of a larger RNA molecule previously identified to be involved in an RNA-protein interaction, or (2) an RNA molecule containing one or more mutations or deletions in a previously identified RNA molecule involved in an RNA-protein interaction, buffer components comprising a buffer, a monovalent cation, a divalent cation, a reducing agent, and a density agent, and non-specific competitors, adding one or more RNA binding proteins, and detecting the interaction between the RNA molecule and the RNA binding proteins. By comparing which RNA molecules interact with the binding proteins to those which do not interact, the region of the RNA molecule involved in the interaction can be identified. An assay of this type can identify all the regions in an RNA molecule involved in an interaction with an RNA binding protein as well as identifying the specific nucleotides that interact with the RNA binding protein.

8. Identifying Regions in RNA Binding Proteins That Interact With RNA Molecules Regions in RNA binding proteins that interact with RNA molecules can be identified by forming a binding solution comprising one or more RNA molecules, buffer components comprising a buffer, a monovalent cation, a divalent cation, a reducing agent, and a density agent, and non-specific competitors, and adding one or more fragments of an RNA binding protein that were obtained by peptidase digestion of an RNA binding protein or by peptide synthesis, and detecting the interactions of the RNA binding protein peptides with the RNA molecules. This is feasible since the portion of an RNA binding protein that interacts with an RNA molecule is generally a self-contained domain. By comparing which peptides are involved in an interaction with an RNA molecule and which are not, the region of the RNA binding protein involved in the interaction can be identified. Identification of the specific amino acids involved in the interaction of the RNA binding protein with the RNA molecules can be accomplished by making mutations in the peptide fragments that interact with the RNA molecules and testing the mutated peptides for interactions with RNA molecules. The amino acids that are involved in the interaction of the RNA binding protein with the RNA molecule will be identified by the mutated peptides that do no interact with the RNA molecule.

9. Screening For Compounds That Modulate Interaction Of RNA Molecules And RNA Binding Proteins Identification of compounds that modulate the interaction of RNA molecules and RNA binding proteins can be accomplished by including one or more test compounds in the binding solution comprising the RNA molecules of interest, the RNA binding proteins of interest, and buffer components, and detecting the interaction between the RNA molecules and the RNA binding proteins. Test compounds that modulate or affect the interaction between the RNA molecules and RNA binding proteins can be identified by comparing the interactions in the binding solution that does not contain the test compound with the interactions in the binding solution containing the test compounds. Binding solutions that include one or more test compounds are referred to herein as test solutions. Binding solutions that do not include a test compound are referred to herein as control solutions. Compounds that modulate the interaction will be identified if the interactions in the two solutions differ. An assay of this type can be used to identify compounds that modulate or affect the interaction by binding to the RNA molecules or by binding to the RNA binding proteins in a given sample. By delivering an identified compound to a cell in which an RNA molecule of interest, or a related RNA molecule, is expressed, the function or action of the RNA molecule in the cell can be affected due to the modulation or effect the compound has on the interaction of the RNA molecule and RNA binding proteins. For example, where an interaction between a mRNA molecule and an RNA binding protein controls the translation of the mRNA, a compound identified as affecting that interaction in the disclosed assay can be used to affect the translation of the mRNA via its effect on the interaction. Identified compounds can be used to affect the function or expression of an RNA molecule in a cell in vivo, ex vivo, or in vitro. The identification of such compounds can also lead to the development of therapies to treat a variety of diseases. Such compounds can also be used as research tools to study the significance, nature, or mechanism of RNA function or expression in a cell.

a. High throughput screening assay. The disclosed universal assay conditions can be used in a screening assay to identify compounds which affect a RNA/RNA binding protein interaction of interest. Such screening assays can be designed to allow simultaneous assessment of the effect of numerous test compounds on the interaction of interest. For this purpose, it is preferred that the interactions be detected by filter binding. Simultaneous filter binding assays are preferably performed by simultaneous filtering of binding solutions in an apparatus having separate wells, holes, slots, or other compartments which can hold separate binding solutions. A preferred form of multi-well filter binding apparatus is the MultiScreen filter plate of Millipore. It is also contemplated that multiple multi-well or multi-sample assays can be performed simultaneously.

In general, high throughput screening can be performed as follows. First, a set of one or more test solutions is formed, where each test solution includes one or more RNA molecules and buffer components. The test solutions are then heated for a time and to a temperature sufficient to denature the RNA molecule(s), and slowly cooled. Next, one or more RNA binding proteins are added to the test solutions, and interactions between the RNA molecule(s) and the RNA binding protein(s) in the test solutions are detected. One of the test compounds is included in the test solution. To determine whether the test compounds have an effect on the interactions between the RNA molecule(s) and the RNA binding protein(s) a control solution is formed, heated, and cooled as with the test solutions, except that no test compound is present in the control solution. The RNA binding protein(s) are added to the control solution, and interactions between the RNA molecule(s) and the RNA binding protein (s) in the control solution are detected. By comparing the interactions detected in the test solutions with those detected in the control solution, it can be determined if a given test compound has an effect on the interactions. A test compound is identified as a compound having an effect on interactions between the RNA molecule(s) and the RNA binding protein (s) if the interactions detected in the control solution and the interactions detected in the test solution containing the test compound differ.

The test compound can be added to the test solution at any time, for example, during formation of the test solution, prior to the heating step, prior to adding the RNA binding protein, or with the RNA binding protein. It is preferred that the test compound is mixed with either the RNA molecule or the RNA binding protein prior to their addition to the test solution.

The assay using the control solution can be performed separately from, or together with, the assays of the test solutions. When performed separately, the control solution assay can be performed either before, after, or simultaneous with the test solution assays. It is preferred that the control solution assay be performed together and simultaneously with the test solution assays.

As used herein a set of test solutions refers to one or more test solutions which are related to each other by having the same RNA binding protein(s), RNA molecule(s), and buffer components. The test solutions within a set of test solutions preferably differ from each other in the test compound present in the test solution. It is contemplated and preferred that a single control solution, or a single form of control solution, be used for comparison of interactions detected in an entire set of test solutions. For this purpose it is preferred that the control solution have the same RNA binding protein (s), RNA molecule(s), and buffer components as the test solutions in the set. Multiple sets of test solutions, and a control solution for each set, can also be assayed together in a high throughput assay. For this purpose it is preferred that either or both of the RNA binding protein's) or the RNA molecule(s) differ between each set of test solutions. For assays involving such multiple sets of test solutions, it is solutions use each set of test solutions use the same set of test compounds.

Preferred relationships between test solutions, sets of test solutions, and control solutions, as described above, can be illustrated with the following schematic examples. In the following examples, different RNA molecules or sets of RNA molecules (a given solution can contain a single RNA molecule or multiple RNA molecules) are referred to R1, R2, R3, etc. Different RNA binding proteins are referred to as P1, P2, P3, etc. Test compounds are referred to as C1, C2, C3, etc. Buffer components, as a group of components in a given solution, are referred to as B1, B2, B3, etc.

Three sets of test solutions, referred to as set 1, set 2, and set 3, are set up using the following components:

|  | Set 1 | Set 2 | Set 3 |
|---|---|---|---|
| RNA | R1 | R2 | R3 |
| Protein | P1 | P2 | P3 |
| Buffer | B1 | B1 | B1 |

For each set, a different control solution is set up using these same components. Thus, each set is designed to assess the effect of test compounds on a different RNA/RNA binding protein interaction (or group of interactions). A different test compound can be included in each test solution in each set as follows:

| Test solution | Set 1 | Set 2 | Set 3 |
|---|---|---|---|
| 1 | C1 | C1 | C1 |
| 2 | C2 | C2 | C2 |
| 3 | C3 | C3 | C3 |
| 4 | C4 | C4 | C4 |
| ... | ... | ... | ... |
| 92 | C92 | C92 | C92 |
| 93 | C93 | C93 | C93 |
| 94 | C94 | C94 | C94 |
| 95 | C95 | C95 | C95 |

No test compound is added to the control solutions. As can be seen, in this example, the same bank of 95 test compounds are tested for an effect on each of the three RNA/ RNA binding protein interactions. Similar groups of assays could be performed using a different set of test compounds, or a partially overlapping set of compounds. The entire group of assays described above can be performed simultaneously and, preferably, is automated. The number of assays in any set of test assays can be increased to accommodate as many test compounds as desired. In such cases, of course, it is preferred that the set of test assays be divided into manageable groups, based on, for example, the number of wells in a multi-well filter apparatus. It is contemplated that the disclosed method can be performed using devices and apparatus designed to accommodate a large number of test assays.

b. Preferred modes of identifying compounds. It is preferred that interactions be detected in an automated manner using, for example, automated detection and comparison of interaction signals. Where the RNA molecule(s) or the RNA binding protein(s) are labeled with a detectable group, it is preferred that interactions be detected using automated quantitative detectable group. For this purpose, it is preferred that the detectable group include a component that produces, either directly or indirectly, a quantifiable signal. Preferred components of this type are radioactive isotopes. Reagents and methods for the use and detection of radioactive labels are well known.

Simultaneous gel shift assays are preferably accomplished by subjecting multiple binding solutions to electrophoresis in a single gel with multiple lanes, and in multiple gels each with multiple lanes. Detection and comparison of multiple samples can be accomplished by, for example automated detection and localization of interacting complexes in the gel lanes.

It is preferred that the test compounds be mixed with either the RNA molecule, either before, during or after formation of the binding solution, or the RNA binding protein prior to addition to the binding solution. For this purpose, it is preferred that the test compound be mixed with either the RNA molecule or the RNA binding protein depending on with which of these components it is desired or expected the test compound will interact. For example, if compounds affecting the interaction of an RNA and an RNA binding protein via interaction with the RNA are desired (or expected, given the nature of the test compounds), then the test compound should be added to the RNA. Conversely, if compounds affecting the interaction of an RNA and an RNA binding protein via interaction with the RNA binding protein are desired (or expected, given the nature of the test compounds), then the test compound should be added to the RNA binding protein. It is most preferred that the test compound be added to the binding solution after heating and cooling and before addition of the RNA binding protein. It is also preferred that all of the test solutions in a given set of test solutions Shave the test compound mixed in the same way and at the same stage for all of the assays.

c. Identified compounds. Compounds identified as having an effect on interactions between RNA molecules and RNA binding proteins can be used to affect such interactions in cells. In the case where the interaction between an RNA molecule and an RNA binding protein affects the function or expression of the RNA molecule, a compound having an effect on the interaction is expected to have an effect on the function or expression of the RNA molecule. Thus, it is contemplated that compounds identified having an effect on the interaction of an RNA molecule and an RNA binding protein will be useful for affecting the function or expression of the RNA molecule in a cell. Such compounds can be delivered to cells in any manner which allows the compound to have the desired effect. Many such modes of delivery are known in the art. A preferred form of delivery for in vivo applications are compositions combining an identified compound and a pharmaceutically acceptable carrier. For this purpose, the disclosed method can include a step of forming such a composition. For in vitro and ex vivo applications, an identified compound can be added to the culture medium. The compound can also be combined with any delivery system or composition that can enhance the entry of the compound into the cell and/or enhance the delivery of the compound to particular cells.

Suitable pharmaceutical vehicles for administration to a patient are known to those skilled in the art. For parenteral administration, the compound can be dissolved or suspended in sterile water or saline. For enteral administration, the compound can be incorporated into an inert carrier in tablet, liquid, or capsular form. Suitable carriers may be starches or sugars and include lubricants, flavorings, binders, and other materials of the same nature. The compound can also be administered locally at a desired site by topical application of a solution or cream.

Alternatively, the compound may be administered in, on or as part of, liposomes or microspheres (or microparticles). Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. No. 4,906,474, 4,925,673, and 3,625,214.

The criteria for assessing response to therapeutic modalities employing an identified compound is dictated by the specific condition and will generally follow standard medical practices. Generally, the effect of administration of a compound can be assessed at least by determining if the RNA/RNA binding protein interaction determined to be affected by the compound is in fact affected in cells to which the compound is administered or delivered. Such an assessment can also be made by determining if there is an effect on a surrogate for the interaction, such as expression of an RNA, production of a protein, or a consequent physiological effect. Where the RNA/RNA binding protein interaction affected by the protein is known or suspected to involve the function or expression of an RNA involved in a disease condition, the effectiveness of administration of the compound can be assessed by measuring changes in characteristics of the disease condition.

EXAMPLES

Example 1

Development of optimum universal assay conditions

Universal conditions for the assay to detect interaction between RNA binding proteins and RNA molecules were optimized using gel mobility shift to detect interactions. The assay was performed generally as described above. Specifically, a binding solution was formed by mixing an RNA binding protein sample, an RNA molecule, and buffer components. The buffer components included a buffer, a monovalent cation, a divalent cation, a reducing agent, and a density agent. The type and concentration of the various buffer components were varied to assess their effect on binding and to determine which composition of the buffer components facilitated interactions of RNA binding proteins with a variety of RNA molecules.

RNA Binding Proteins: A protein extract from SH-SY5Y cells was used as the RNA binding protein sample. Protein extracts have also been prepared and tested from numerous other cell lines including HeLa, K562 and primary astrocytes and from tissue samples, for example, rat brain. The SH-SY5Y extract was prepared as follows. A sample of SH-SY5Y cells was divided into 10 large cultures 30 ml each in T150 flasks ($9.9 \times 10^5$ cells/flask). The media was removed, the cells were washed in 1× PBS, and scraped in PBS. The cells were then counted as follows: ($.73 \times 10^4$ cells/ml) ×(42 ml)×(10 (×dilution))=$3.1 \times 10^8$ cells total. After counting, the PBS was removed and 400 μl lysis buffer (per dish) was added. The lysis buffer had the following composition:

| 10 ml | stock concentration | final concentration |
| --- | --- | --- |
| 250 μl | 1 M Tris HCl (pH 7.9) | 25 mM Tris-HCl (pH 7.9) |
| 20 μl | 50 mM EDTA | 0.5 mM EDTA |
| 100 μl | 10 mM PMSF | 0.1 mM phenylmethyl sulfonyl fluoride |
| 100 μl | 200 mM sodium fluoride | 2 mM sodium fluoride |
| 100 μl | 200 mM sodium pyrophosate | 2 mM sodium pyrophosate |

The cells were then frozen at −20° C. for 30 minutes, thawed, and centrifuged at 15000 g at 4° C. for 15 minutes. The supernatant was divided into 100 μl aliquots and stored at −80° C.

RNA Molecules: AUUUA, amyloid precursor protein (APP) untranslated region (UTR), and poly(A) were used as the RNA molecules in separate assays. These were chosen to assess the ability of the assay to detect interactions using disparate RNA molecules. The RNA molecules were prepared by in vitro transcription by SP6 or T7 RNA polymerase. To facilitate detection of interactions, $^{32}$P-UTP was incorporated into the RNA molecules during transcription. Many in vitro transcription kits are commercially available and optimized for efficient RNA synthesis. The RNA molecules were prepared generally as described by Sambrook et al. and Ausubel et al. Briefly, a reaction mix containing 2 µl 10× transcription buffer (400 mM Tris-HCl, pH 7.5, 60 mM MgCl$_2$, 20 mM spermidine, 50 mM NaCl), 1 µl each of ATP, CTP, and GTP (10 mM), 2 µl 50 µM UTP, 2.5 µl $^{32}$P-UTP, 2 µl linear transcription template (approximately 100 ng) and 2 µl enzyme mix (RNase Inhibitor and 20 U RNA polymerase) was prepared in a final volume of 20 µl. Unless otherwise indicated, all dilutions were made with DEPC treated water. This reaction mixture was incubated for 2 hours at 37° C. Then 1 µl of RNase-free DNase I was added and the reaction incubated for 15 minutes at 37° C. The unincorporated nucleotides are then removed by gel filtration through G-25 spin columns.

Optimizing Buffer: The first variable in the assay is the buffer. Tris, HEPES, and Bis-Tris Propane (BTP), were tested for efficiency at promoting interactions with the test RNA molecules. For these assays the buffer was at a concentration of 7.5 mM and the binding solution included 10 mM KCl, 0.2 mM DTT, 10% glycerol, and 0.2 µg/µl tRNA as competitor for non-specific RNA/protein interactions. Protein was added at a concentration of 1 µg/µl. Assays were also performed to determine the optimum pH for the buffer. The buffers studied were HEPES at pH 8, Bis-Tris Propane at pH 8 and 7.5, and Tris at pH 8 and pH 7.4. All three buffers allowed for the binding interaction for all three RNA molecules. While there was little difference between them, the use of BTP resulted in significant binding in all cases and, since it has the largest range of buffering capacity, was chosen as the buffer for further optimization.

For all RNA molecules studied, the optimal pH appeared to be 8 or 9. Significant binding was observed for each RNA molecule at pH 10, a condition in which RNase T$_1$ inhibition becomes evident. Conversely low pH seems to inhibit binding. The results are summarized in the table below:

|        | pH |    |    |    |    |
| ------ | -- | -- | -- | -- | -- |
| RNA    | 6  | 7  | 8  | 9  | 10 |
| APP    | −  | −  | +  | ++ | ++ |
| AUUUA  | −  | ++ | ++ | ++ | ++ |
| poly(A)| −  | ++ | ++ | ++ | +  |

Based on these results, the preferred assay will be composed of RNase T$_1$, tRNA as the non-specific competitor, and a buffer consisting of BTP at pH 8.5.

Optimizing Cations: The final aspect of kit development was the optimization of monovalent and divalent cations. Three monovalent (K$^+$, Na$^+$, and NH$_4^+$) and three different divalent cations (Mg$^{++}$, Ca$^{++}$, and Fe$^{++}$) were analyzed. These were tested at various concentrations (0, 0.1, 1, 10, 50, 100 and 250 mM). The optimal monovalent cation was then tested with the individual divalent cation concentrations and vice versa.

Three monovalent (K$^+$, Na$^+$, and NH$_4^+$) cations were first tested at concentrations ranging from 0 to 500 mM. Initially, 0, 0.2, 2, 12.5, 20, and 50 mM concentrations of each cation were tested for effects on RBP/RNA complex formation for APP, AUUUA, and poly(A). The SH-SY5Y protein extract and a binding buffer consisting of 20 mM Bis-Tris propane at pH 9.0, previously demonstrated to result in optimal binding interactions, were used in addition to the cation and probe. No significant differences were noted for either concentration or cations at 0 to 50 mM. Higher concentrations were then tested.

The studies of divalent cation effects of RBP/RNA interactions were also initiated. The concentration effect of Mg$^{++}$ on the complex formation between APP RNA and proteins (SH-SY5Y) was examined first. The results showed that at lower concentrations ($\leq$10 mM) of Mg$^{++}$, normal complex formation was observed. At higher concentrations (10 mM, 50 mM, 100 mM, 250 mM) Mg$^{++}$ inhibited the interaction between APP RNA and proteins to differing degrees.

The wide concentration range of monovalent cations capable of promoting interactions compared to the relatively narrow range for divalent is likely due to APP adapting tertiary structures which depend on divalent cations. This would suggest that AUUUA and poly(A) interactions may not be as dependent on divalent cations since they are presumably linear structures.

The concentration effects of divalent cations (Mg$^{++}$, Ca$^{++}$ and Fe$^{++}$) on the complex formation between APP, AUUUA and poly(A) RNA and proteins (SH-SY5Y) were then examined. The results demonstrated that 1 mM for all three divalent cations is the optimal concentration for the detection of interactions between RNAs (APP, AUUUA and poly(A)) and proteins (SH-SY5Y) under the selected binding condition. At higher concentration (10 mM, 50 mM, 100 mM, 250 mM), Mg$^{++}$, Ca$^{++}$ and Fe$^{++}$ inhibited the complex formation to varying degrees. Following a comparison of all three divalent cations at the optimal concentration for binding interactions (1 mM), Mg$^{++}$ was selected for further studies.

The effects of individual monovalent salt concentrations (0, 50, 100, and 500 mM) on AUUUA, APP, and poly(A) RNA's binding to SH-SY5Y protein were also completed. The monovalent cations used were K$^+$, Na$^+$ and NH$_4^+$. RNA-protein complexes form in a much broader monovalent salt concentration (0 to 100 mM) than was observed for the divalent cations (0 to 5 mM) with the optimal monovalent salt concentration being determined to be 50 mM. The binding interaction with the cis-element of APP for all three monovalent cations was compared at 50 mM and KCl was chosen based on its ability to promote the RBP/RNA interaction.

The monovalent (K$^+$) and divalent (Mg$^{++}$) cations were then combined to determine the best concentrations used in the development of the detection kit. Combinations of 10, 50 and 100 mM K$^+$ with 1 mM Mg$^{++}$ and 0.1 mM, 1 mM, and 2.5 mM Mg$^{++}$ with 50 mM K$^+$ were analyzed. The results showed that the combination of 50 mM K$^+$ with 1 mM Mg$^{++}$ is better than the other combinations for detecting APP RNA-protein interactions. This result was confirmed by using AUUUA RNA and poly(A) RNA.

Use of Reducing Agents: The effects of reducing agents were studied by comparing the binding reaction under the previously established conditions (0.2 mM DTT), substituting 0.2 mM β-mercaptoethanol for the DTT, or in the absence of a reducing agent. In five of the six interactions studied, the presence or absence of reducing agent had no effect on the binding interaction. Similarly, no effect of reducing agent was observed with poly(A) RNA and binding protein derived from K562 cells. However, when binding protein was isolated from HeLa cells, a reproducible effect was observed with DTT enhancing the interaction better than β-mercaptoethanol which in turn was better than no reducing agent. The requirement of DTT for certain reactions suggests that its use is preferred as a component of the buffer.

Use of Density Agents: The binding efficiencies of six different RNAs were tested in the presence of 10% glycerol, 10% polyethylene glycol, or no density agent, under buffer, cation and reducing conditions described above. Although no quantitative differences were detected, the addition of glycerol or PEG enhanced the quality of the band on the gel mobility assay. In the absence of a density agent the bands were clearly more diffuse. Thus, while not required, the addition of 10% glycerol is preferred.

Based on this work, the optimal buffer components were determined to be BTP at pH 8.5, 50 mM KCl, 1 mM $MgCl_2$, 0.2 mM, DTT and 10% glycerol. These conditions have been used for further validating assays as described below. A BTP concentration of 7.5 mM was used.

Heating Step: The next phase involved screening twelve other RNA elements for detection of interactions under the selected conditions. These assays were also run in the presence of specific and non-specific competitor RNA. The first two cis-elements studied were the Iron Response Element (IRE) and histone RNA. In each case, binding was detected but very inefficiently. Since these had been reported to form secondary structures, we heated the labeled RNA to 80° C. and then cooled the sample to 37° C. after forming the binding solution and before adding the RNA binding proteins. This was intended to break any incorrect structures that may have formed in the RNA and it greatly facilitated the detection of interactions. For both cis-elements specific interactions were detected under our conditions. RNAs of various sizes and structures have been tested under the above conditions and shown to form interactions with binding proteins consistent with those reported in the literature. The binding proteins tested contain various motifs, including RGG boxes, KH domains and Arg-rich proteins.

The preferred method for detecting interactions between RNA molecules and RNA binding proteins involves (1) forming a binding solution including RNA molecules, BTP at pH 8.5, 50 mM KCl, 1 mM $MgCl_2$, 0.2 mM DTT, and 10% glycerol, (2) heating the binding solution to denature the RNA molecules, (3) cooling the binding solution, (4) adding RNA binding proteins to the binding solution, and (5) detecting the interactions between the RNA molecules and the RNA binding proteins.

Example 2
Assays Using Universal Conditions

Several assays were performed demonstrating the usefulness of the universal assay conditions described in Example 1 for detecting interactions between various RNA molecules and RNA binding proteins. In the first assay, interactions of several RNA molecules (radioactively labeled) with different recognition features were incubated with SH-SY5Y or CHL/260 protein extract. The RNA molecules were chosen to highlight detection of interactions dependent on RNA sequence (AUUUA RNA), sequence and RNA structure (histone RNA), or RNA structure alone (double-stranded RNA). In addition to these small RNA molecules (less than 30 nucleotides), the 210 nucleotide 5' untranslated region of glucose transporter type 1 (Glut1) was also tested. SH-SY5Y protein extract was used with AUUUA RNA and CHL/260 protein extract was used with the remaining RNA molecules. The gel contained multiple slower migrating bands in each of the lanes. This indicates that the universal assay conditions allow detection of interactions between RNA molecules and RNA binding proteins across the spectrum of interaction types.

In another assay, interactions of several RNA molecules representing targets for different binding motifs were incubated with SH-SY5Y or CHL/260 protein extract or recombinant Rev protein. The RNA molecules were chosen to highlight detection of interactions involving RNA binding proteins containing double-stranded RNA binding motifs (IRE-BF), RGG box (APP-BF), Arg-rich motifs (RRE-BF), and RNP motifs (U1-BF). SH-SY5Y protein extract was used in the APP-BF assay, CHL/260 protein extract was used with the IRE-BF and U1-BF assays, and recombinant Rev protein was used with the RRE-BF assay. The gel contained multiple slower migrating bands in each of the lanes. This indicates that the universal assay conditions allow detection of interactions between RNA molecules and RNA binding proteins across the spectrum of interaction types.

In another assay, the specificity of the interaction being detected was confirmed. Radioactively labeled IRE RNA was incubated in the presence or absence of K562 protein extract. To test whether interactions detected were specific or not, unlabeled IRE was also included in some of the assays. This RNA competes with the labeled IRE RNA for interaction with RNA binding proteins. As a control, unlabeled mutant IRE (which is defective for binding) was included in some assays. If the interaction is specific, this RNA should not compete with the labeled IRE RNA for the RNA binding proteins. In gel lanes for assays where no protein extract was included, no mobility shift is vivible, as expected. In gel lanes for assays where protein extract was included, a clear mobility shift is visible. In assays where increasing concentrations (100×, 1,000×, and 10,000×, respectively) of unlabeled IRE RNA was included, the unlabeled RNA effectively competes with the labeled RNA for interaction with the RNA binding proteins at the 1,000×, and 10,000× concentrations. In assays where increasing concentrations (100×, 1,000×, and 10,000×, respectively) of mutant IRE RNA was included, the unlabeled RNA is unable to compete with the labeled RNA for interaction with the RNA binding proteins. This clearly indicates that the competitive effect of unlabeled IRE RNA is not due to non-specific interactions between the RNA molecules and the RNA binding proteins.

The universal assay conditions are also beginning to be used in high throughput screening assays for compound isolation. Such assays will analyze combinatorial libraries for compounds capable of altering the binding properties of the RBP to the RNA, with the RNA being targeted. The information obtained from RNA mapping and peptide mapping will be used in molecular modeling to rationally design compounds capable of modulating the interaction of the RNA binding protein with the RNA molecule.

Example 3
Development of High-Throughput Screening Assay

The following assays demonstrate modes and the effectiveness of the disclosed high throughput screening assay. All binding reactions were performed in 96-well v-bottom plates in a final volume of 10 $\mu$l. The assays were constituted and performed as described below. Specifically, assays were performed by (1) forming a binding solution including RNA molecules, 7.5 mM BTP at pH 8.5, 10 mM KCl, 5 mM $MgCl_2$, 0.2 mM DTT, and 10% glycerol, (2) heating the binding solution to denature the RNA molecules, (3) cooling the binding solution, (4) adding RNA binding proteins to the binding solution, (5) loading the binding solution onto a filter, and (6) detecting the amount RNA retain on the filter. It is preferred that the samples be loaded on to a filter of either pure nitrocellulose or a mixed cellulose ester (MCA). It is also preferred that the filters have a 0.2$\mu$ pore size, although filters with a 0.45$\mu$ pore size will also bind the RNA/RNA binding protein complex. It is preferred that, prior to loading the binding solution onto a filter, the volume is increased. For this purpose, it is preferred that the dilution solution has the same buffer components as the binding solution except lacking the density agent. For a 10 μl volume it is preferred that the final volume be about 100 μl. It is also preferred that the binding solution be loaded onto the filter under vacuum. It is also preferred that the filter is washed twice prior to detecting the amount of RNA retained on the filter. Preferably the wash solution had the same composition as the dilution solution. However, TE (pH 8.0), PBS, or TCA can also be used as wash solutions. In most of the assays described below, the RNA molecules were labeled with $^{32}$P.

The nitrocellulose filter plate was precoated with bovine serum albumin (BSA), polyvinylpyrrolidone (PVP), polyG, polyI, polyC, polyU or tRNA as a blocking agent prior to loading the assay solutions. Regardless of whether the well was untreated or precoated with a blocking agent, the free RNA cpms (that is, RNA retained on the filter in the absence of RNA binding protein measured in radioactive counts per minute (cpm)) were 7 to 12% of the protein-bound cpms. This indicates that blocking is not required or preferred.

Optimizing Protein Concentration

Results from gel mobility shifts demonstrate that not all the RNA added to the reaction is shifted by 2 μg of protein extract, thus protein titrations were carried out to maximize the number of counts detected so that there will be a greater difference range for detection of active compounds. This was also expected to increase the ratio of bound:free RNA. The amount of protein extract (SH-SY5Y or K562, depending on which RNA was used) was titrated from 1 to 10 μg protein per reaction in increments of 1 μg. The results were, for all RNA/protein combinations tested (APP/SH-SY5Y; IRE/K562; AUUUA/K562; nAChR/SH-SY5Y; His/K562, U1/K562; Glut-1/K562), a concentration-dependent rise in protein-bound cpms up to roughly 5 to 7 μg, where the reaction reached a plateau and decreased slightly through 10 μg. Taken together, these results indicate that the optimal concentration of protein extract is greater than about 0.5 μg/μl. The data is summarized in Table 1. It was found in most cases that the half maximal concentration for wild-type binding was in the 2 to 4 μg range. It is preferred that the amount of protein extract used in the screen be in to 2 to 4 μg range to facilitate detection of compounds that both enhance or inhibit the RNA/RNA binding protein interaction. When labeled mutant RNAs were tested they also produced detectable counts, but the absolute number of cpms bound are 5 to 100 times lower than for wild-type RNAs.

TABLE 1

| Probe | Plateau | Half maximal conc. |
|---|---|---|
| His-WT | 7 μg (n = 14, 7 w/T1, 7 w/o T1) | 3.7 μg (w/ or w/o T1) |
| His-MUT | 4.8 μg (n = 3) | 2.7 μg |
| AUUUA | 8 μg (n =2, w/ or w/o T1) | 4 μg (w/o T1), 2.25 μg (w/T1) |
| U1-WT | 5 μg (n = 8) | 2 μg |
| U1-MUT | 7 μg (n = 4) | 2 μg |
| Glut-1 | 8.25 μg (n = 2) | 2.4 μg (w/o T1), 3 μg (w/T1) |
| IRE-WT | 5 μg (n = 6) | 1.5 μg |
| IRE-MUT | 5 μg (n = 4) | 3 μg |
| APP | 5 μg (n = 1) | 2 μg |

Competition Assays

To test the ability of the filter assay to detect changes in binding activity (that is, decreased interaction between RNA and RNA binding proteins) competition assays were performed with IRE RNA and K562 protein extract (see FIG. 1). Competition experiments were performed by adding increasing concentrations (100 to 10,000×) of unlabeled wild-type or mutant IRE RNA to the binding reaction. FIG. 1 illustrates the results. A concentration dependent inhibition of binding was observed in assays in which the unlabeled wild-type RNA was added whereas no competition was observed in assays in which unlabeled mutant RNA was added.

Figure 2:
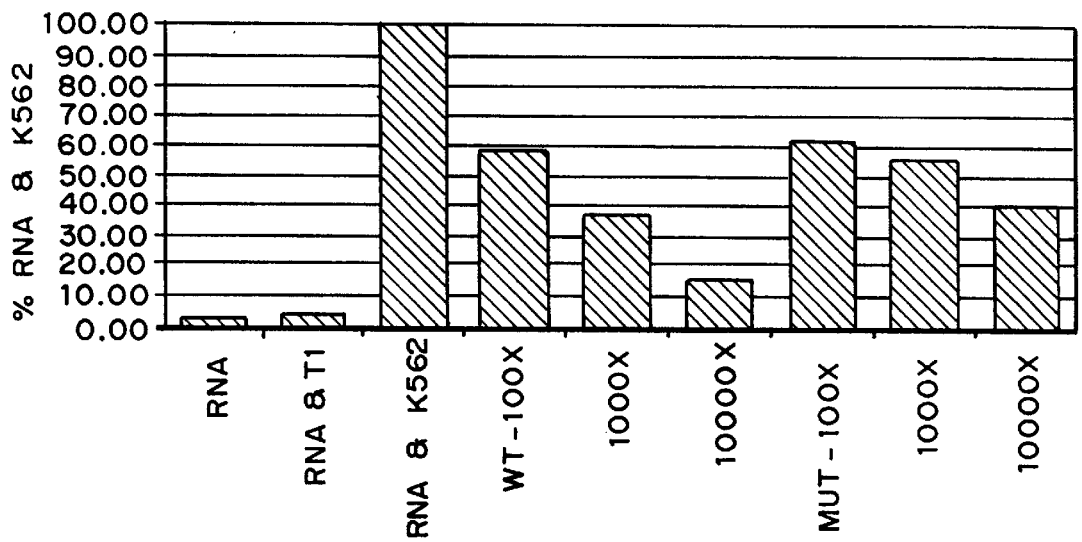
FIG. 2 is a graph of the amount of radioactively labeled RNA retained on a filter (expressed in percent of the amount of RNA retained on a filter in a reference binding solution) following loading of various binding solutions. All of the binding solutions contained radioactively labeled U1 RNA either alone or including various other components. The first two columns represent binding solutions without RNA binding protein. The remaining columns represent binding solution containing RNA binding protein (K562 extract). WT indicates that the binding solution included the indicated amount of unlabeled wild type RNA as a competitor. MUT indicates that the binding solution included the indicated amount of unlabeled mutant RNA as a competitor. In this instance, the U1 mutant interacts with less affinity than does the wild type sequence.

To more fully test the filter assay, competitions were performed with U1 and His RNAs as well. Both U1 and His wild-type RNAs showed a concentration dependent inhibition of binding (see FIG. 2.). However, the mutant RNAs also inhibited binding in a concentration dependent manner, although at about 10-fold higher concentration. FIG. 2 illustrates these results for the U1 competition. In these competition assays, unlike the IRE assay, the mutant RNA used has been shown to bind the RNA binding protein, although with a lower affinity than the wild-type RNA. The results of the U1 and His filter assay competitions reflect the ability of the assay to detect low affinity as well as higher affinity binding interactions.

Modulation of the Binding Interaction by Small Molecules

Binding assays were performed with wild-type IRE RNA and K562 protein extract in the presence of sources of iron or iron chelators to determine the ability of the filter assay to detect the modulation of binding interactions by small molecules. Increasing concentrations of the iron sources hemin (1 to 100 μM) and FeCl$_3$ (1 μM to 1 mM) or the iron chelator desferroxiamine (1 μM to 1 mM) were added to the binding reactions (see FIG. 3). Hemin and FeCl$_3$ produced a concentration-dependent inhibition of binding. Desferroxiamine did not change the amount IRE/protein complex formed, perhaps because there is not enough iron in the cell extract to produce a noticeable change upon addition of desferroxiamine. The reactions were analyzed by gel shifts to visualize the results of the filter assay.

Exploratory Library Screen

A 96 member exploratory compound library that contained CNI-1493, a compound previously shown to post-transcriptionally inhibit TNF-α production, was generated. The library was initially screened at 10 μM against $^{32}$P-labeled AUUUA RNA. Several methods of introducing the compounds into the binding reaction were tested. Initially the compounds were co-incubated with the RNA and protein, producing modest results. Next, preincubation with either the protein extract or the RNA was tried with improved results.

Figure 5:
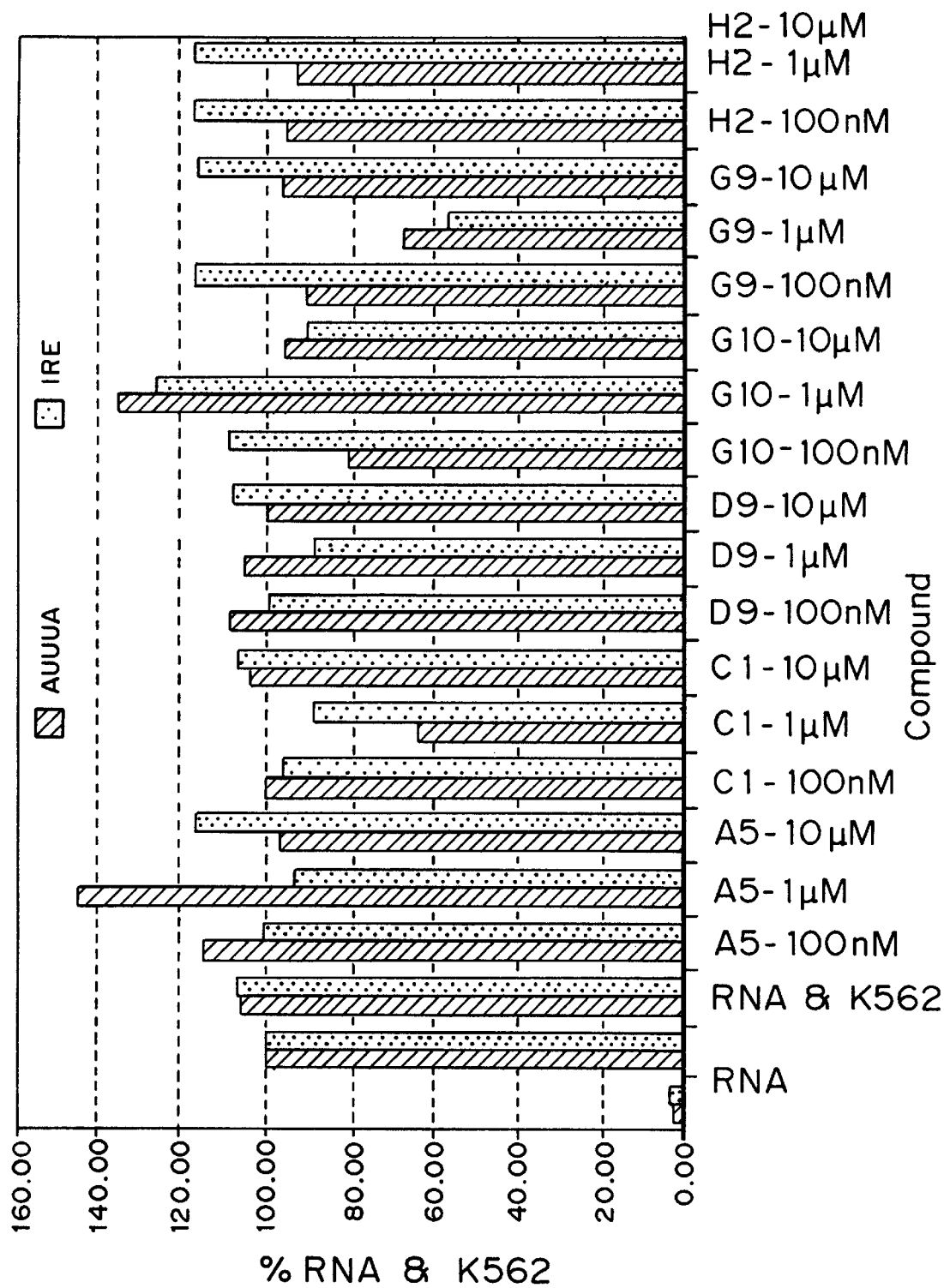
FIG. 5 is a graph of the amount of radioactively labeled RNA retained on a filter (expressed in percent of the amount of RNA retained on a filter in a reference binding solution) following loading of various binding solutions. Alternate columns correspond to binding solutions containing radioactively labeled AUUUA RNA or IRE RNA, either alone or including various other components. The first two column represents binding solutions without RNA binding protein. The remaining columns represent binding solution containing RNA binding protein (K562 extract). Columns 5 through 40 correspond to binding solutions including the indicated amount of the indicated test compound.

Seventeen compounds were chosen for further analysis at 100 nM, 1 μM and 10 μM using both AUUUA and IRE RNAs based on the results from three screening efforts (Exps. 29–31). Table 2 summarizes the results from these compounds at 10 μM. The results are also shown graphically in FIG. 4. Compound Cl was consistently the most active inhibitor resulting in close to a 50% reduction in counts (p=0.001) while A5 was the most active enhancer increasing counts by 38% over controls (p<0.001). Compound G10, CNI-1493, produced a substantial increase in counts in 3 of the 4 experiments. Compounds D9 and H2, chosen as negative controls from the initial screening, continued to have no effect in the dose dependent screen (Exp. 33) and were identified as vehicle controls. When the 17 compounds were screened against IRE RNA, a differential effect was seen with compound A5 (see FIG. 5). This most efficacious enhancer of AUUUA binding failed to have an effect on IRE.

TABLE 2

| Compound | Experiment # | | | | Compound | Avg. % | SEM |
| --- | --- | --- | --- | --- | --- | --- | --- |
| | #33 | #31 | #30 | #29 | | | |
| RNA | 1.84 | 2.57 | 1.98 | 1.48 | RNA | 1.97 | 0.28 |
| RNA&K562 | 100.00 | 100.00 | 100.00 | 100.00 | RNA&K562 | 100.00 | |
| A3-10 μM | 103.79 | 67.58 | 92.35 | 82.69 | A3-10 μM | 86.60 | 7.69 |
| A4-10 μM | 104.74 | 93.36 | 62.58 | 98.27 | A4-10 μM | 89.74 | 9.35 |
| A5-10 μm | 144.10 | 145.00 | 133.15 | 130.31 | A5-10 μm | 138.14 | 3.75 |
| A11-10 μm | 101.75 | 96.59 | 76.95 | 82.91 | A11-10 μm | 89.55 | 5.78 |
| C1-10 μm | 64.52 | 39.48 | 43.08 | 68.93 | C1-10 μm | 54.00 | 7.44 |
| C8-10 μm | 104.98 | 79.45 | 85.32 | 79.37 | C8-10 μm | 86.53 | 6.42 |
| D9-10 μm | 105.10 | 105.54 | 100.69 | 99.68 | D9-10 μm | 102.75 | 1.50 |
| E7-10 μm | 99.20 | 87.16 | 74.40 | 93.46 | E7-10 μm | 88.56 | 5.32 |
| F6-10 μm | 100.10 | 82.17 | 57.89 | 85.68 | F6-10 μm | 81.46 | 8.76 |
| G1-10 μm | 89.62 | 80.62 | 94.23 | 80.16 | G1-10 μm | 86.16 | 3.46 |
| G6-10 μm | 91.49 | 85.57 | 92.72 | 80.41 | G6-10 μm | 87.55 | 2.85 |
| G7-10 μm | 94.62 | 82.06 | 62.38 | 79.87 | G7-10 μm | 79.73 | 6.63 |
| G9-10 μm | 68.52 | 81.48 | 74.65 | 67.25 | G9-10 μm | 72.98 | 3.26 |
| G10-10 μm | 135.24 | 127.28 | 66.94 | 114.53 | G10-10 μm | 111.00 | 15.29 |
| G11-10 μm | 93.50 | 87.91 | 88.39 | 85.17 | G11-10 μm | 88.74 | 1.74 |
| G12-10 μm | 93.56 | 86.39 | 86.37 | 84.10 | G12-10 μm | 87.60 | 2.06 |
| H2-10 μm | 93.39 | 97.31 | 103.77 | 95.65 | H2-10 μm | 97.58 | 2.20 |

Analysis

Competition studies have been performed using the filter assay in which unlabeled wild-type or mutant RNA is added to the reaction at 100 to 10,000 times the concentration of $^{32}$P-RNA to compete for the protein binding of the radiolabeled RNA. It has been demonstrated the high-throughput assay can be used effectively for this type of study using a variety of RNA molecules including IRE, AUUUA, APP, U1, and His. Using IRE, a concentration dependent inhibition of binding by unlabeled wild-type RNA has been shown, with no effect of shown by unlabeled mutant RNA, except at the highest concentration. These results have been confirmed by gel shift analysis. Furthermore, the disclosed assay can be used to detect more subtle differences in the ability of various RNA molecules to bind protein as demonstrated by the results of the U1 and His experiments. In this case, the mutant RNA has a weak binding affinity for the RNA binding protein. When unlabeled mutant RNA is added to the binding reaction, a slight concentration dependent inhibition is detected with maximum inhibition of 50 to 70% occurring at 10,000 times the $^{32}$P-RNA concentration. In this way, the binding affinity of various altered forms of the binding site of an RNA binding protein can be compared.

A 96 member random compound library was screened with the disclosed high throughput assay. The compounds were initially screened at 10 μM against $^{32}$P-labeled AUUUA RNA. One compound was found to produce a significant increase in detectable counts while two compounds were found to produce a significant decrease in counts. Seventeen compounds were chosen for further analysis at 100 nM, 1 μM and 10 μM using both AUUUA and IRE RNA molecules to determine if any selectivity of the compounds could be detected. When the 17 compounds were screened against IRE RNA, a differential effect was seen with the enhancing compound. The most efficacious enhancer of AUUUA binding failed to have an effect on IRE. Gel shifts of these compounds using AUUUA RNA confirmed the activity of the inhibitors.

Example 4
Identification of RNA Binding Protein Binding Sites

The following examples illustrate manners of identifying putative binding sites for RNA binding proteins present in a nucleotlide sequence database and confirmation that some identified nucleotide sequences do interact with RNA binding proteins.

The GenBank nucleotide sequence database was searched for the presence of the sequence for CD45, a cell surface protein implicated in lymphatic activation. A term search using the Entrez program from NCBI revealed 13 sequences, of which 4 were human. The human sequences were chosen for further analysis in part because such human sequences are of most practical interest. In general, human sequences identified in such searches are preferred. Of the four sequences meeting the above criteria, two of the sequences (Accession numbers M23461 and M23499) contained the sequence of the full-length 5' UTR as demonstrated by both primer extension and S1 nuclease protection. The nucleotide sequence of this UTR is shown in SEQ ID NO:4.

A second term search of GenBank with Entrez for C4b-binding protein, which controls activation of the complement cascade, resulted in the identification of 83 sequences, 66 of which were from human. Comparison of the human sequences and information entered by the submitters allowed us to define the 5' UTR. The start of the UTR was predicted to be nucleotide 381 (Accession number of M62448) based on comparison of the 5' ends of the mRNAs submitted and the localization of CAAT signals in the above-referenced submission. The nucleotide sequence of this UTR is shown in SEQ ID NO:3.

A primer pair was designed from the 5' end of the UTR and a 3' primer encompassing nucleotide +1 with the use of the OLIGO program. Similar primers encompassing the same criteria can be designed either manually without the use of this program, or using another similar oligonucleotide design program. In addition, the 5' primer contained 24 nucleotides at the 5' end encoding for the T7 promoter. Clones containing the above sequences were generated by rtPCR from total RNA obtained from the K562 lymphoblastoma cell line. The clones were restriction mapped and analyzed by gel electrophoresis to confirm their identity.

PCR products generating a single band (in the undigested lanes) were then used for in vitro transcription of labeled RNA using Ambion's Maxiscript Kit. The labeled transcripts were used in the RNA binding protein detection assay described above. The binding solutions containing the labeled RNA were incubated with 2 μg of protein isolated from the same cell from which the rtPCR product was generated, and the products were resolved on a non-denaturing gel. Labeled UTRs which exhibit binding activity were then used in a second experiment to demonstrate specificity of the interaction. In this experiment, a 100 and 1,000 fold molar excess of unlabeled identical RNA or the same excess of different RNA are added to the binding reactions. For both CD45 and C4b-binding protein, a concentration dependent inhibition of complex formation was observed with specific competitor while no competition was seen when the mutant IRE RNA was added in excess.

Those skilled in the art will recognize, or be able to ascertain using no more than routine experimentation, many equivalents to the specific embodiments of the invention described herein. Such equivalents are intended to be encompassed by the following claims. The references cited herein are hereby incorporated by reference.

We claim:

1. A nucleic acid molecule comprising a nucleotide sequence,
    wherein the nucleotide sequence is operatively linked to heterologous sequences, wherein the nucleotide sequence is SEQ ID NO:1, SEQ ID NO:2, SEQ ID NO:3, SEQ ID NO:4, the corresponding DNA sequence of SEQ ID NO:1, the corresponding DNA sequence of SEQ ID NO:2, the corresponding DNA sequence of SEQ ID NO:3, or the corresponding DNA sequence of SEQ ID NO:4.

2. The nucleic acid molecule of claim 1 wherein the nucleic acid molecule consists of the nucleotide sequence.

3. A nucleic acid molecule comprising a nucleotide sequence,
    wherein the nucleotide sequence is not operatively linked to a protein encoding nucleotide sequence to which the nucleotide sequence is naturally linked,
    wherein the nucleotide sequence is SEQ ID NO:1, SEQ ID NO:2, SEQ ID NO:3, SEQ ID NO:4, the corresponding DNA sequence of SEQ ID NO:1, the corresponding DNA sequence of SEQ ID NO:2, the corresponding DNA sequence of SEQ ID NO:3, or the corresponding DNA sequence of SEQ ID NO:4.

4. The nucleic acid molecule of claim 3 wherein the nucleic acid molecule is an RNA molecule or can be transcribed into an RNA molecule, wherein the RNA molecule does not contain a protein encoding nucleotide sequence to which the nucleotide sequence is naturally linked.

5. The nucleic acid molecule of claim 4 wherein the nucleic acid molecule is an RNA molecule.

6. A nucleic acid molecule consisting of the nucleotide sequence identified as SEQ ID NO:1, SEQ ID NO:2, SEQ ID NO:3 or SEQ ID NO:4.

7. The nucleic acid molecule of claim 1 wherein the nucleic acid molecule is an RNA molecule or can be transcribed into an RNA molecule, wherein the RNA molecule does not contain a protein encoding nucleotide sequence to which the nucleotide sequence is naturally linked.

* * * * *

UNITED STATES PATENT AND TRADEMARK OFFICE
CERTIFICATE OF CORRECTION

PATENT NO. : 5,859,227
DATED : January 12, 1999
INVENTOR(S) : Tony Giordano, Deborah L. Beach, David Jacobs It is certified that error appears in the above-identified patent and that said Letters Patent is hereby corrected as shown below:

On the title page: Item [56]

In other publications, Herbert, A., et al. reference, replace "strranded" with --stranded--;

At col. 5, line 12, replace "interest The" with --interest. The--;

At. col. 5, line 59, replace "dithiotlireitol" with --dithiothreitol--;

Column 7, line 48, replace "$^{251}I$" with --$^{125}I$--;

Column 10, line 10, replace "(HMG, CoA Red)" with --(HMG CoA Red)--;

UNITED STATES PATENT AND TRADEMARK OFFICE
CERTIFICATE OF CORRECTION

PATENT NO. : 5,859,227

DATED : January 12, 1999

INVENTOR(S) : Tony Giordano, Deborah L. Beach, David Jacobs

It is certified that error appears in the above-identified patent and that said Letters Patent is hereby corrected as shown below:

Column 16, line 60, replace "binding" with --Binding--;

Column 19, line 50, replace "protein's)" with --protein(s)--;

Column 21, line 14, replace "Shave" with --have--;

Column 22, line 46, replace ".73" with --73--;

Column 25, line 12, replace "0.2 mM, DTT" with --0.2 mM DTT--.

Signed and Sealed this

Seventh Day of December, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 272 base pairs
( B ) TYPE: nucleic acid
( C ) STRANDEDNESS: single
( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| GGGGCGGGCC | AATGGCGGCG | GTCCTATAAA | AAGGCAGCTC | CGCGCGCTCT | CTTCCTAAGA | 60 |
| ACACAAGAAT | CCCTTGTGGA | GTGTCGGTTT | AGGTTGCAGG | GTCTTAAGTG | AGTCAGGGCG | 120 |
| CGGAGGTCCG | GCGGGAGACG | CATAGTCACA | GAACGTCCAT | TCTCCGTTTC | ACAGCCCGCA | 180 |
| CAGCTTGAGC | CTCGAGCGCA | GCGCGGCCAT | GGAGCCCAGC | AGCAAGAAGG | TGACGGGCCG | 240 |
| CCTTATGTTG | GCCGTGGGAG | GGGCAGTGCT | CG | | | 272 |

( 2 ) INFORMATION FOR SEQ ID NO:2:

( i ) SEQUENCE CHARACTERISTICS:
( A ) LENGTH: 108 base pairs
( B ) TYPE: nucleic acid
( C ) STRANDEDNESS: single
( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:2:

| | | | | | | |
|---|---|---|---|---|---|---|
| UCCUUCCGCU | CCGCGACUGC | GUUAACUGGA | GCCAGGCUCA | GCGUCGGCGC | CGGGGUUCGG | 60 |
| UGGCCUCUAG | UGAGAUCUGG | AGGAUCCAAG | GAUUCUGUAG | CUACAAUG | | 108 |

( 2 ) INFORMATION FOR SEQ ID NO:3:

( i ) SEQUENCE CHARACTERISTICS:
( A ) LENGTH: 107 base pairs
( B ) TYPE: nucleic acid
( C ) STRANDEDNESS: single
( D ) TOPOLOGY: linear ( i i ) MOLECULE TYPE: RNA ( i i i ) HYPOTHETICAL: NO -continued (iv) ANTI-SENSE: NO (xi) SEQUENCE DESCRIPTION: SEQ ID NO:3:

| GCUGCUUUAU | UUCUGCUGUU | AAUCAUUCAU | UGGGCCCGUC | AAAAGUUUCU | GCCCAUCUAU | 60 |
| UUCCAUCAAC | CGUCCUUGAC | CAGCCAACCA | CAUGGCUGAA | AUUCAGG | | 107 |

(2) INFORMATION FOR SEQ ID NO:4:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:4:

| CUGACAUCAU | CACCUAGCAG | UUCAUGCAGC | UAGCAAGUGG | UUUGUUCUUA | GGGUAACAGA | 60 |
| GGAGGAAAUU | GUUCCUCGUC | UGAUAAGACA | ACAGUGGAGA | AAGGACGCAU | GCAGUUUCUU | 120 |
| AGGGACACGG | CUGACUUCCA | GAUAUGACCA | UGUAUUUGUG | GCUUAAACUC | UUGG | 174 |